(12) United States Patent
Hughes et al.

(10) Patent No.: US 9,901,268 B2
(45) Date of Patent: Feb. 27, 2018

(54) SENSOR, CIRCUITRY, AND METHOD FOR WIRELESS INTRACRANIAL PRESSURE MONITORING

(75) Inventors: Kevin Hughes, Oreland, PA (US); Alexander Strachan, Verona, NJ (US)

(73) Assignee: Branchpoint Technologies, Inc., Irvine, CA (US)

( * ) Notice: Subject to any disclaimer, the term of this patent is extended or adjusted under 35 U.S.C. 154(b) by 1381 days.

(21) Appl. No.: 13/446,068

(22) Filed: Apr. 13, 2012

(65) Prior Publication Data

US 2012/0265028 A1   Oct. 18, 2012

Related U.S. Application Data

(60) Provisional application No. 61/475,216, filed on Apr. 13, 2011.

(51) Int. Cl.
*A61B 5/03* (2006.01)
*A61B 5/11* (2006.01)
*A61B 5/00* (2006.01)

(52) U.S. Cl.
CPC ............... *A61B 5/031* (2013.01); *A61B 5/11* (2013.01); *A61B 5/1117* (2013.01); *A61B 5/6864* (2013.01); *A61B 5/6868* (2013.01); *A61B 2562/0219* (2013.01); *A61B 2562/0247* (2013.01); *A61B 2562/0261* (2013.01); *A61B 2562/046* (2013.01); *A61B 2562/168* (2013.01)

(58) Field of Classification Search
CPC .... A61B 2562/0219; A61B 2562/0247; A61B 2562/0261
See application file for complete search history.

(56) References Cited

U.S. PATENT DOCUMENTS 3,434,090 A   3/1969 Chelner
3,757,770 A   9/1973 Baryshaw et al.
(Continued)

FOREIGN PATENT DOCUMENTS

JP   2002-010986 A   1/2002
JP   2005-512663 A   5/2005
(Continued)

OTHER PUBLICATIONS

International Search Report/Written Opinion dated Feb. 19, 2013, in counterpart PCT Application No. PCT/US2012/059182.
(Continued)

*Primary Examiner* — Adam J Eiseman
(74) *Attorney, Agent, or Firm* — Knobbe Martens Olson & Bear LLP

(57) ABSTRACT

An intracranial pressure monitoring device includes a housing defining a first internal chamber, a plurality of strain gauges disposed on an inner surface of a diaphragm defined by a wall of the first internal chamber, a device for generating orientation signals, and circuitry coupled to the plurality of strain gauges and to the device. The circuitry is configured to generate intracranial pressure data from signals received from the plurality of strain gauges, generate orientation data based on the orientation signals received from the device, and store the intracranial pressure data and the orientation data in a computer readable storage such that the intracranial pressure data and orientation data are associated with each other.

30 Claims, 19 Drawing Sheets

(56) References Cited

U.S. PATENT DOCUMENTS

| | | |
|---|---|---|
| 4,014,319 A | 3/1977 | Favre |
| 4,026,276 A | 5/1977 | Chubbuck |
| 4,062,354 A | 12/1977 | Taylor et al. |
| 4,080,653 A | 3/1978 | Barnes, Jr. et al. |
| 4,114,603 A | 9/1978 | Wilkinson |
| 4,114,606 A | 9/1978 | Seylar |
| 4,127,110 A | 11/1978 | Bullara |
| 4,147,161 A | 4/1979 | Lkebe et al. |
| 4,186,749 A | 2/1980 | Fryer |
| 4,206,762 A | 6/1980 | Cosman |
| 4,237,900 A | 12/1980 | Schulman et al. |
| 4,246,908 A | 1/1981 | Inagaki et al. |
| 4,265,252 A | 5/1981 | Chubbuck et al. |
| 4,281,666 A | 8/1981 | Cosman |
| 4,354,506 A | 10/1982 | Sakaguchi et al. |
| 4,385,636 A | 5/1983 | Cosman |
| 4,471,786 A | 9/1984 | Inagaki et al. |
| 4,494,411 A | 1/1985 | Koschke et al. |
| 4,519,401 A | 5/1985 | Ko et al. |
| 4,600,013 A | 7/1986 | Landy et al. |
| 5,291,899 A | 3/1994 | Watanabe et al. |
| 5,573,007 A | 11/1996 | Bobo |
| 5,579,774 A | 12/1996 | Miller et al. |
| 5,993,395 A | 11/1999 | Shulze |
| 6,113,553 A | 9/2000 | Chubbuck |
| 6,231,524 B1 | 5/2001 | Wallace et al. |
| 6,234,973 B1 | 5/2001 | Meader et al. |
| 6,248,080 B1 | 6/2001 | Miesel et al. |
| 6,409,674 B1 | 6/2002 | Brockway et al. |
| 6,533,733 B1 | 3/2003 | Ericson et al. |
| 6,673,022 B1 | 1/2004 | Bobo |
| 6,731,976 B2 | 5/2004 | Penn et al. |
| 6,855,115 B2 | 2/2005 | Fonseca et al. |
| 6,897,788 B2 | 5/2005 | Khair et al. |
| 6,950,699 B1 | 9/2005 | Manwaring et al. |
| 7,025,727 B2 | 4/2006 | Brockway et al. |
| 7,122,007 B2 | 10/2006 | Querfurth |
| 7,198,602 B2 | 4/2007 | Eide |
| 7,212,864 B2 | 5/2007 | Wahlstrand et al. |
| 7,245,117 B1 | 7/2007 | Joy et al. |
| 7,335,162 B2 | 2/2008 | Eide |
| 7,347,822 B2 | 3/2008 | Brockway et al. |
| 7,425,200 B2 | 9/2008 | Brockway et al. |
| 7,481,774 B2 | 1/2009 | Brockway et al. |
| 7,621,878 B2 | 11/2009 | Ericson et al. |
| 7,780,679 B2 | 8/2010 | Bobo |
| RE42,378 E | 5/2011 | Wolinsky |
| 8,016,763 B2 | 9/2011 | Eide |
| 8,109,899 B2 | 2/2012 | Sundström et al. |
| 8,237,451 B2 | 8/2012 | Joy et al. |
| 8,343,068 B2 | 1/2013 | Najafi et al. |
| 8,454,701 B2 | 6/2013 | Devauchelle et al. |
| 8,457,744 B2 | 6/2013 | Janzig et al. |
| 8,506,514 B2 | 8/2013 | Pedersen et al. |
| 9,232,921 B2 | 1/2016 | Bobo |
| 2002/0151816 A1 | 10/2002 | Rich et al. |
| 2005/0061079 A1* | 3/2005 | Schulman ............ A61B 5/0031 73/715 |
| 2005/0203438 A1 | 9/2005 | Manwaring et al. |
| 2006/0025704 A1 | 2/2006 | Stendel et al. |
| 2006/0206037 A1 | 9/2006 | Braxton |
| 2007/0088223 A1 | 4/2007 | Mann et al. |
| 2007/0244411 A1 | 10/2007 | Jeng et al. |
| 2008/0139959 A1* | 6/2008 | Miethke ............... A61B 5/0031 600/561 |
| 2008/0161659 A1 | 7/2008 | Reichenberger et al. |
| 2008/0262319 A1 | 10/2008 | Reichenberger et al. |
| 2008/0269573 A1 | 10/2008 | Najafi et al. |
| 2009/0143656 A1 | 6/2009 | Manwaring et al. |
| 2009/0143696 A1 | 6/2009 | Najafi et al. |
| 2009/0203983 A1 | 8/2009 | Carlton et al. |
| 2009/0216149 A1 | 8/2009 | Neff et al. |
| 2010/0030103 A1 | 2/2010 | Lutze et al. |
| 2010/0063542 A1* | 3/2010 | van der Burg ..... A61B 17/0401 606/232 |
| 2010/0121213 A1 | 5/2010 | Giftakis et al. |
| 2010/0161004 A1 | 6/2010 | Najafi et al. |
| 2010/0204589 A1 | 8/2010 | Swoboda et al. |
| 2010/0217108 A1 | 8/2010 | Tauber et al. |
| 2011/0009716 A1 | 1/2011 | Gohler et al. |
| 2011/0066072 A1 | 3/2011 | Kawoos et al. |
| 2011/0071457 A1 | 3/2011 | Raman |
| 2011/0224595 A1* | 9/2011 | Pedersen ................ A61B 5/031 604/8 |
| 2013/0041271 A1 | 2/2013 | Ben-Ari et al. |
| 2015/0297103 A1 | 1/2015 | Hu et al. |
| 2016/0066803 A1 | 3/2016 | Hu et al. |

FOREIGN PATENT DOCUMENTS

| | | |
|---|---|---|
| JP | 2009-112839 A | 5/2009 |
| WO | WO 02/05710 | 1/2002 |
| WO | WO 03/053234 | 7/2003 |

OTHER PUBLICATIONS

Extended European Search Report dated Oct. 13, 2015 in patent application No. 12873949.7.

Fujiwara et al., Oct. 1, 1989, Impact-induced intracranial pressure caused by an accelerated motion of the head or by skull deformation: an experimental study using physical models of the head and neck, and ones of the skull, Forensic Science International, 43(2):159-169.

Yanagida et al., Apr. 1, 1989, Differences in the intracranial pressure caused by a 'blow' and.or a 'fall'—An experimental study using physical models of the head and neck, Forensic Science International, 41(1-2):135-145.

\* cited by examiner

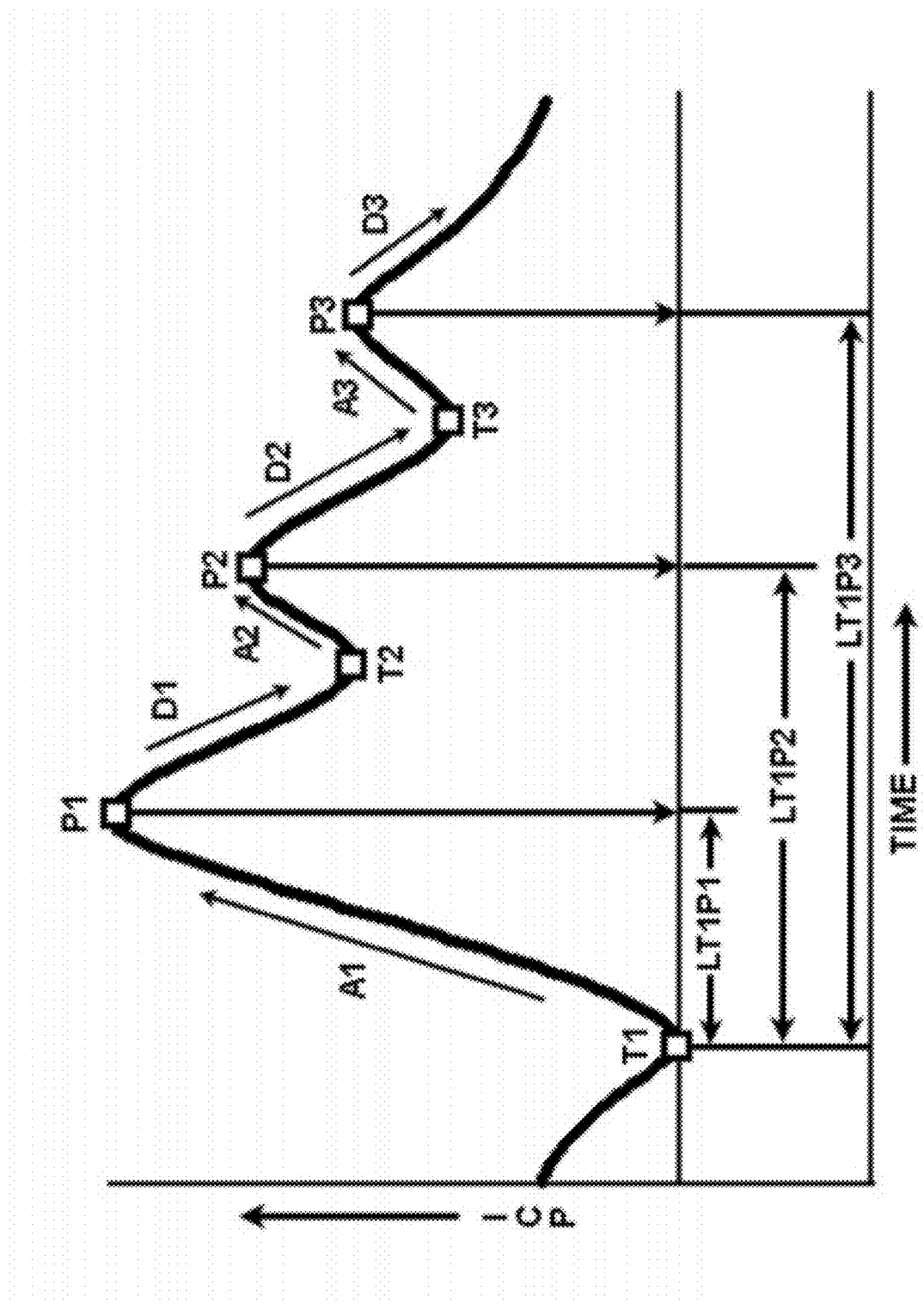

SENSOR, CIRCUITRY, AND METHOD FOR WIRELESS INTRACRANIAL PRESSURE MONITORING

CROSS-REFERENCE TO RELATED APPLICATIONS

This application claims priority to U.S. Patent Application No. 61/475,216 filed on Apr. 13, 2011, the entirety of which is herein incorporated by reference.

BACKGROUND

The disclosed systems and methods relate to extradural pressure monitors for monitoring and storing values related to intracranial pressure. The disclosed devices can be implanted in a head of a patient for either short- or long-term monitoring. The transmission of stored or real-time data to an external device consists of a radio-frequency communication circuit in the device.

Intracranial pressure rises in the settings of a number of acute insults to the brain including trauma, stroke, swelling, hemorrhage, and hydrocephalus. Currently there does not exist a wireless device that measures intracranial pressures reliably and safely. Such a device would improve monitoring in the hospital setting and would furthermore enable intracranial pressure monitoring in the outpatient setting.

Existing intracranial pressure ("ICP") monitoring devices have significant shortcomings which make them impractical for stable and accurate monitoring of intracranial pressure for the long term. Most designs involve either externalization of a fluid column or tunneling a wire connection to an external monitor. As such methods leave an open tract between the external environment and the brain, the likelihood of infection is high.

Additionally, existing ICP devices have significant technical shortcomings. For example, many ICP devices are centered around gauges having a capacitance that varies with pressure, which are measured or sensed by LC circuits having a resonance that varies with this capacitance change. This approach, however, typically suffers from a great deal of drift in the gage readings.

Some designs involve measuring volume changes in a fixed amount of a trapped fluid, which, lacking adequate temperature compensation, make the device's readings subject to both bodily and environmental temperature changes. Additionally, previous designs' methods of transmitting data have been insufficient, as they have been slow, noisy, and inconsistent.

SUMMARY

An intracranial pressure monitoring device includes a housing defining a first internal chamber, a plurality of strain gauges disposed on an inner surface of a diaphragm defined by a wall of the first internal chamber, a device for generating orientation signals, and circuitry coupled to the plurality of strain gauges and to the device. The circuitry is configured to generate intracranial pressure data from signals received from the plurality of strain gauges, generate orientation data based on the orientation signals received from the device, and store the intracranial pressure data and the orientation data in a computer readable storage such that the intracranial pressure data and orientation data are associated with each other.

BRIEF DESCRIPTION OF THE DRAWINGS

FIG. 13 is a cross-sectional view of an intracranial pressure monitoring device installed within a skull of a patient.

DETAILED DESCRIPTION

The disclosed intracranial pressure ("ICP") monitoring devices and methods advantageously enable the short- or long-term monitoring and storage of ICP data in an implanted monitor capable of transmitting this data to an external reader. The disclosed devices have improved drift characteristics and lower infection risks. The disclosed devices and methods enable performing statistical signal analysis on the measured ICP data for purposes of assisting the clinical diagnosis. The data acquired by the device can be transmitted via a fast, reliable, radio frequency communication circuit.

The disclosed devices include low drift, matched semiconductor strain gauges, which transduce deflection in the sensing portion of the device. In some embodiments, the sensing portion of the device is a fixed-edge extended-ridge diaphragm constructed in such a way as to cause the strain in the diaphragm at the location of the ends of the strain gages to be optimal for their drift characteristics.

In some embodiments, the devices are powered by a mechanism, such as a battery, by an inductive coil in combination with a capacitor, or both, which allows for maximum flexibility of operation. The device also conserves power by putting the microprocessor and peripheral electronics into low-power modes between measurements, reducing their overall power draw.

Figure 1:
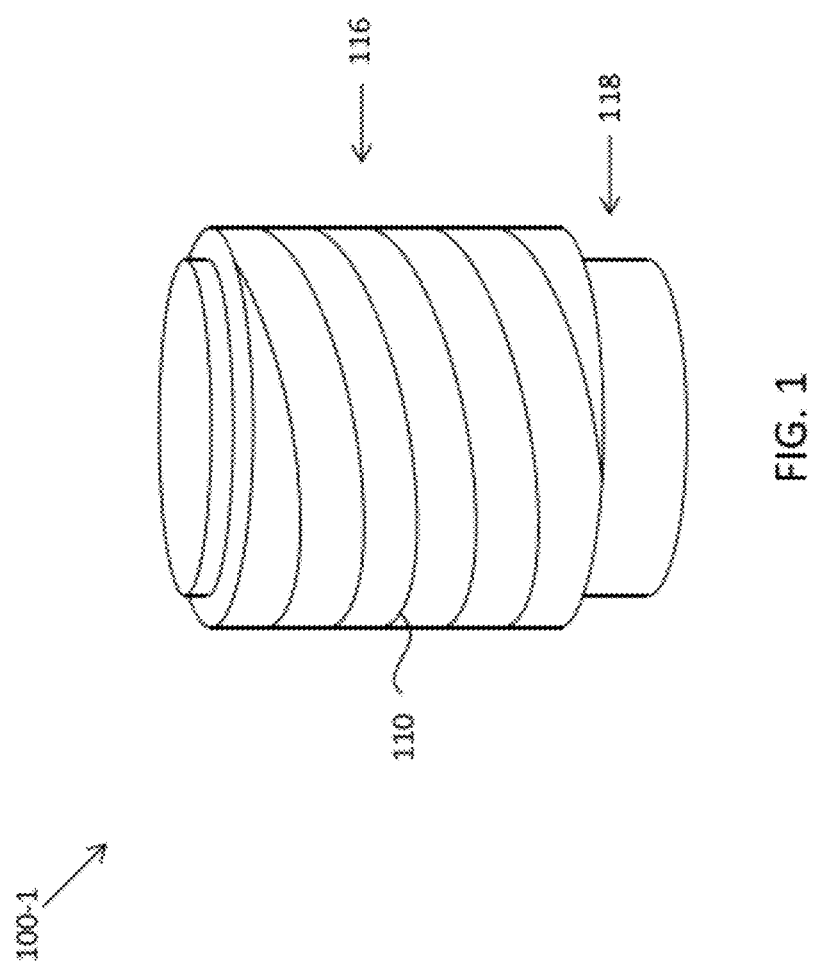
FIG. 1 is a front isometric view of one example of an intracranial pressure monitoring device.
Figure 5:
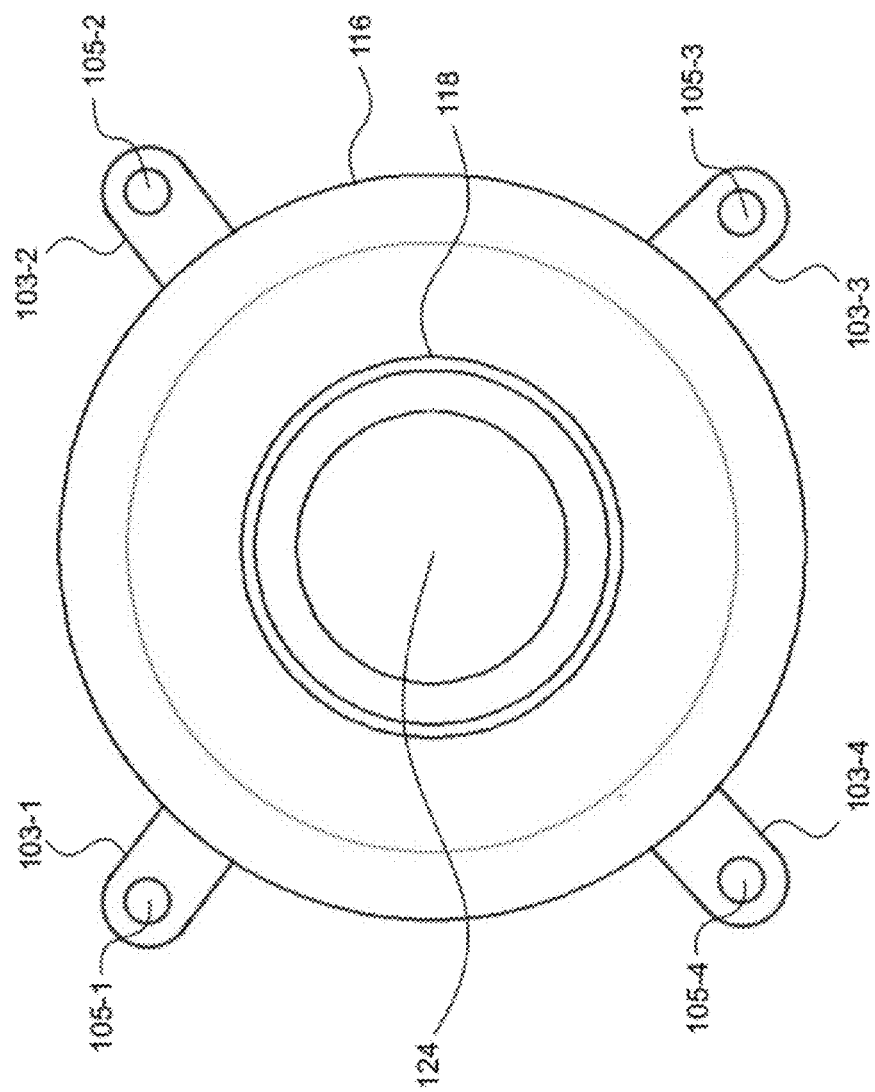
FIG. 5 is a bottom-side plan view of one example of an intracranial pressure monitoring device in accordance with some embodiments.
Figure 6:
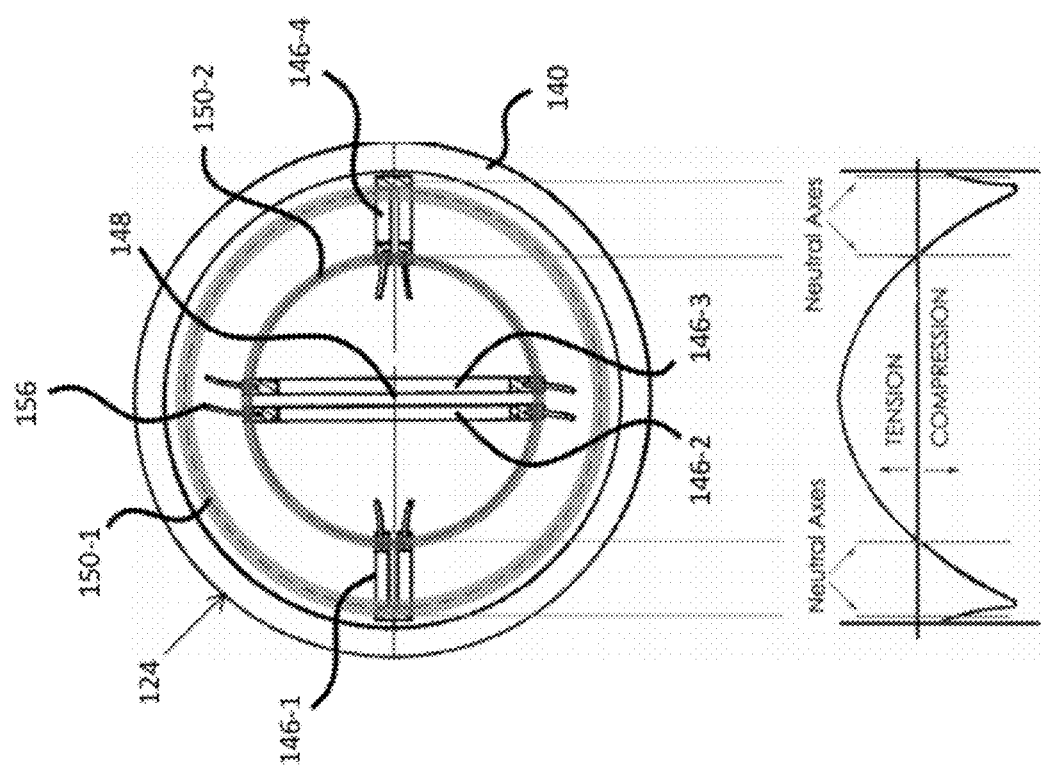
FIG. 6 illustrates one example of a layout of strain gauges disposed on the sensing diaphragm of an improved intracranial pressure monitoring device.

FIG. 1 illustrates one example of an ICP monitoring device 100-1 includes a housing 102 extending from a distal end 104 to a proximal end 106. In some embodiments, housing 102 has a circular cross-sectional area as best seen in FIGS. 1, 5 and 6 and is formed from a metal such as, for example, titanium, stainless steel, gold, silver, or other biocompatible metal. Although housing 102 of ICP monitoring device 100-1 is described as having a circular cross-sectional geometry, one of ordinary skill in the art will understand that housing 102 may have other geometries.

Figure 2:
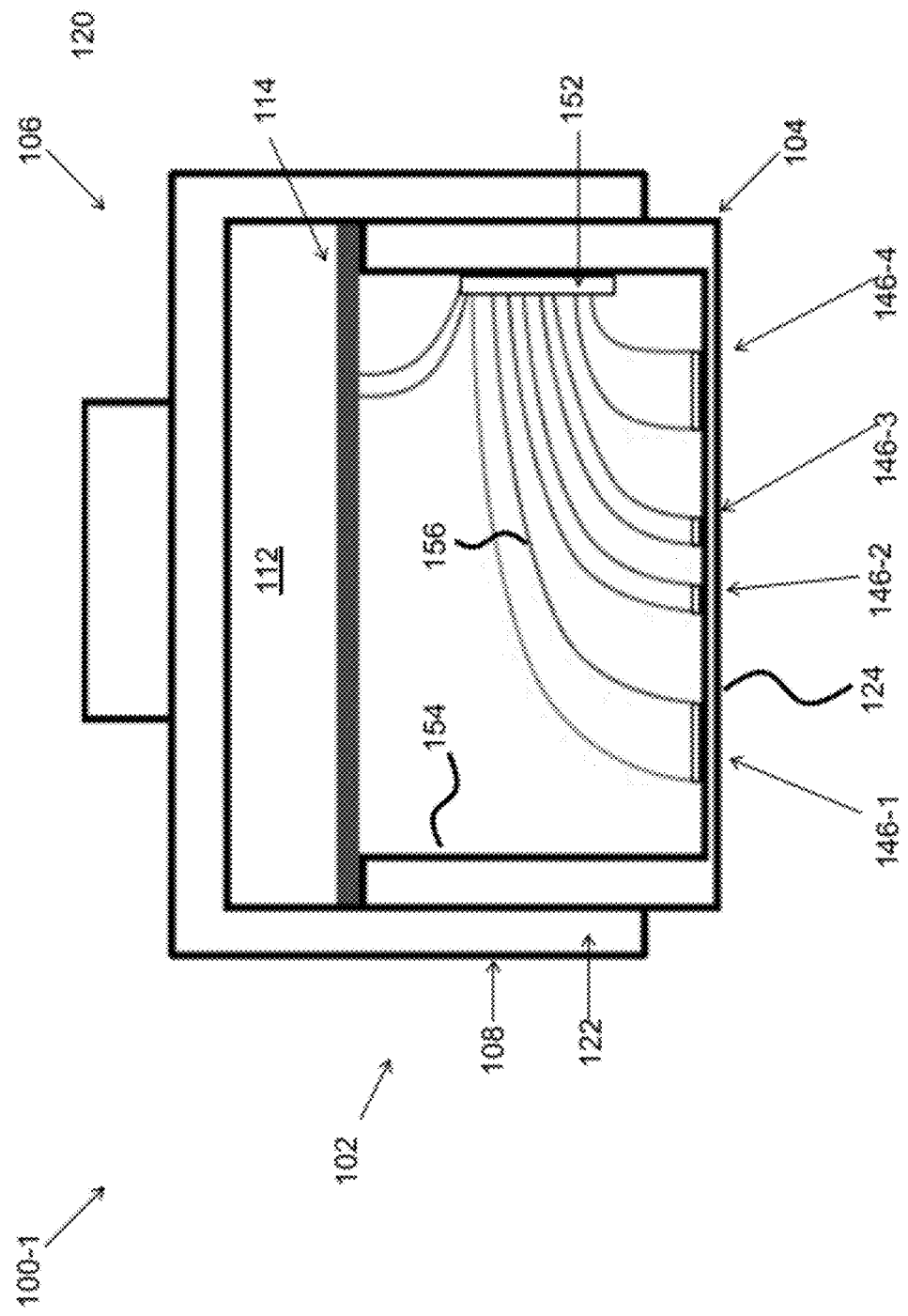
FIG. 2 is a cross-sectional view of the intracranial pressure monitoring device illustrated in FIG. 1.
Figure 3:
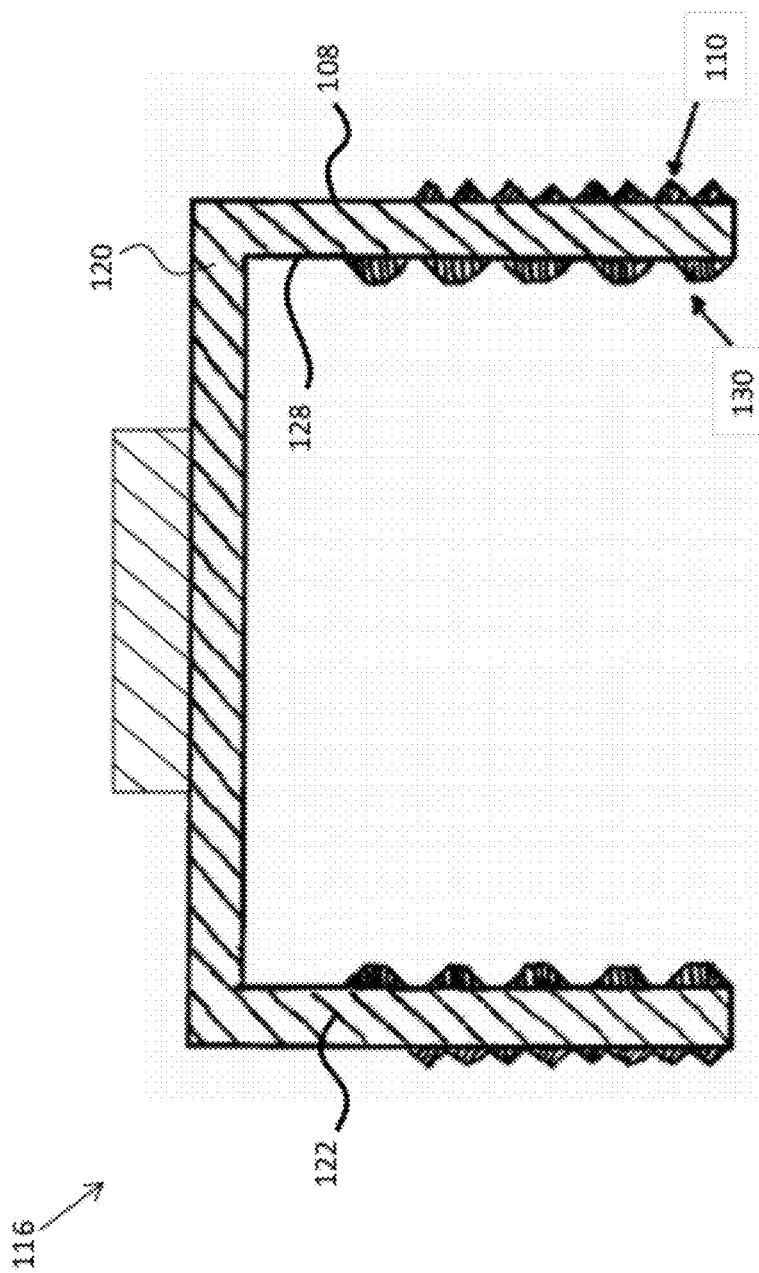
FIG. 3 is a cross-sectional view of the proximal portion of the intracranial pressure monitoring device illustrated in FIG. 1.

As shown in FIGS. 1-3, a portion of the exterior surface 108 of housing 102 includes self-tapping threads 110 for securing ICP monitoring device 100 to the skull of a patient. In some embodiments, such as the bottom side view illustrated in FIG. 5, the exterior surface 108 of housing 102 does not include threads and is instead coupled to the skull of a patient via a press fit and/or through the use of one or more outwardly extending tabs 103-1, 103-2, 103-3, 103-4 (collectively "tabs 103") each defining a respective hole 105-1, 105-2, 105-3, 105-4 (collectively "holes 105") for receiving a screw, which is used for securement. Although four tabs 103 and holes 105 are illustrated in FIG. 5, one of ordinary skill in the art will understand that the number of tabs 103 and holes 105 may be greater than or less than four.

Housing 102 defines an internal chamber 112 (FIG. 2) in which a printed circuit board ("PCB") 114 is disposed. In some embodiments, such as the embodiment illustrated in FIG. 2, housing 102 includes a proximal component 116 that is coupled to a distal component 118. As shown in FIGS. 2 and 3, proximal component 116 includes a chamber sealing wall 120 from which a circular side wall 122 extends in a first direction.

Figure 4:
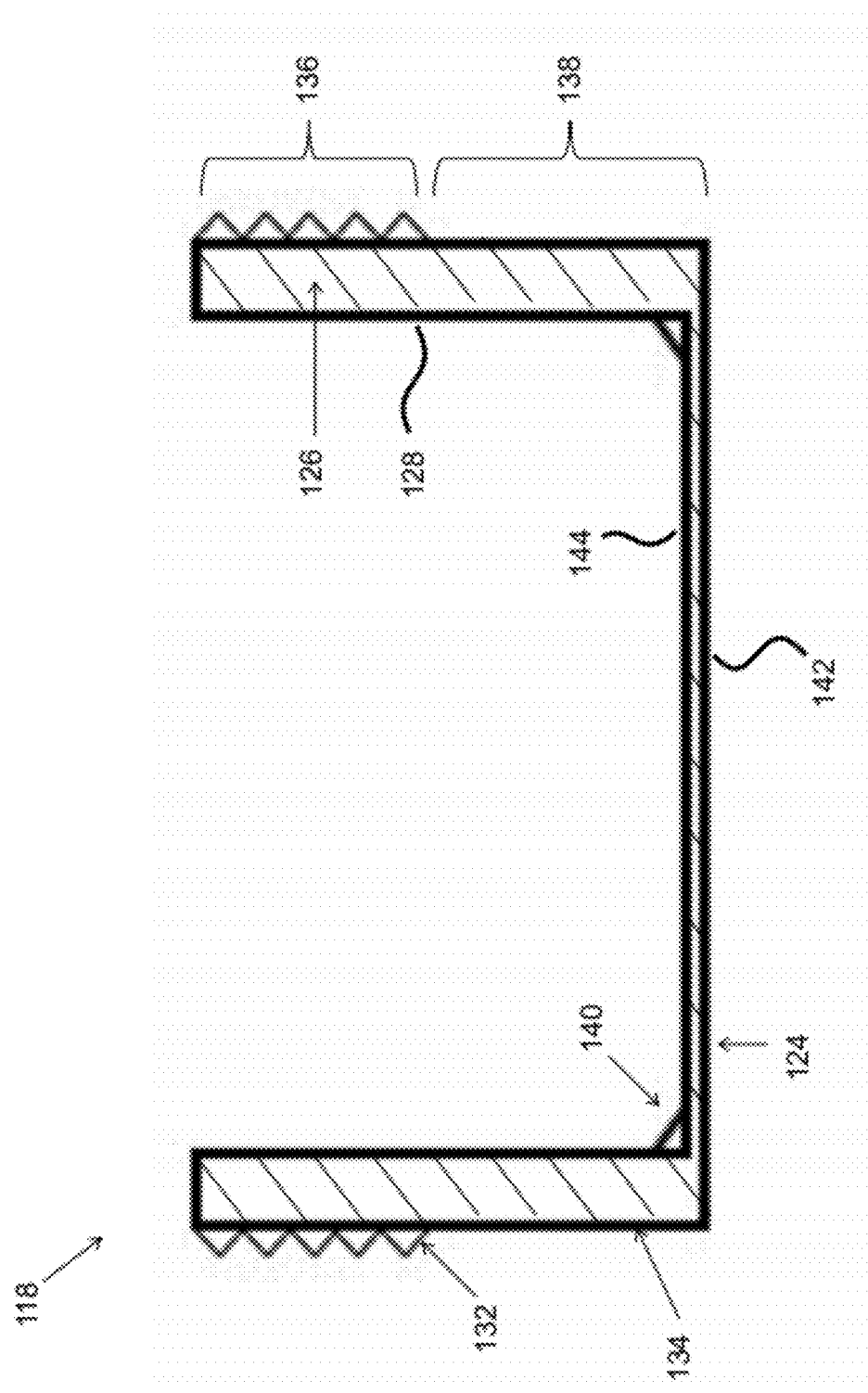
FIG. 4 is a cross-sectional view of the distal portion of the intracranial pressure monitoring device illustrated in FIG. 1.

Distal component 118, which is best seen in FIGS. 2 and 4, includes a bottom wall 124, which defines a fixed-edge diaphragm as described in greater detail below, from which circular side wall 126 extends.

Proximal component 116 and distal component 118 are coupled together to provide a hermetic seal such that chamber 112 has an internal pressure, which is known. In some embodiments, chamber 112 has a pressure that is lower than all anticipated pressures expected to be exerted on bottom wall 124 during normal operating conditions when ICP monitoring device 100-1 is implanted in a skull of a patient. Sealing chamber 112 at a known pressure that is lower than expected operating pressures mitigates the possibility of an effect known to those of ordinary skill in the art as "oil-canning," in which a transition from concave to convex conformations, or vice versa, induces erroneous gauge readings and signal noise.

In some embodiments, chamber 112 is filled during manufacturing with a gas such as Argon, Helium, or other combination of gases. In some embodiments, chamber 112 is filled with an electrically insulating liquid or is evacuated prior to sealing. The effect of controlling the contents of the sealed chamber 112 is to create a reference pressure against which the degree of deformation of the fixed-edge diaphragm may be measured in order to correlate to an external pressure experienced by the diaphragm. Controlling the contents of sealed chamber 112 also controls and defines the characteristic pressure changes in the chamber contents, which affects the gauges and pressure readings as the temperature changes.

In some embodiments, the internal surface 128 of side wall 122 of proximal component 116 defines one or more threads 130 that are configured to engage one or more threads 132 disposed on the external surface 134 of side wall 126 of distal component 118. In some embodiments, threads 132 are formed on a first portion 136 of side wall 126 that is less than an entire length of side wall 126 such that portion 138 is unthreaded. Portion 138 is left unthreaded to isolate fixed-edge diaphragm 124 from heat and stress concentrations induced during the threading process.

Bottom wall 124, which defines the fixed-edge diaphragm, comprises an impermeable, sealed diaphragm that is configured to interface with the dural sac, pial layer, brain parenchyma, or cerebro spinal fluid as described below. A ridge 140 extends between and forms the interface between side wall 126 and bottom wall 124. Ridge 140 extends at a non-perpendicular angle with respect to side wall 126 and bottom wall 124 to change the stress concentrations as described below. In some embodiments, the thickness of bottom wall 124 is between 0.004 inches and 0.005 inches, although one of ordinary skill in the art will understand that bottom wall 124 may have other thicknesses. The thickness of side wall 126 may be varied although it should be sufficiently thick to withstand stresses from manufacturing and induced stress from being under pressure in situ.

In some embodiments, the external surface 142 of bottom wall 124, which forms the diaphragm, is electro-polished or coated with materials or drugs known to prevent scar tissue overgrowth. Fibrous tissue overgrowth occurs within several weeks of implantation of foreign material into the body. While the formation of scar tissue overgrowth is a normal part of the body's physiological healing response, it is typically undesirable as it can affect pressure transmission across diaphragm 124. Additionally, contraction of such scar tissue can artificially deform or generate pressures on the diaphragm. Examples of materials that may be deposited on external surface 142 include, but are not limited to, polyvinylpyrrolidone ("PVP"), phosphoryl colene, polyethylene oxide ("PEO"), hydro-gels, and paralene, to name a few possible materials. Examples of drugs that may be disposed on the external surface 142 of bottom wall 124 includes, but are not limited to, anti-inflammatory agents, cell cycle inhibitors, anti-platelet agents, anti-thrombin compounds, and thrombolytic agents.

External surface 142 is fabricated to provide a flat surface. As will be understood by one of ordinary skill in the art, a flatter diaphragm 124 is less compliant and thus the electrical changes induced in gauges 146 mounted on the diaphragm 124 will have a higher gain than from a less flat diaphragm. Thus, a flat diaphragm minimizes the dampening effects of tissue overgrowth by enabling more sensitive gauge measurements.

The internal surface 144 of bottom wall 124 may support one or more strain gauges 146-1, 146-2, 146-3, and 146-4

("strain gauges 146"). Strain gauges 146 may be connected to bottom wall 124 using an epoxy or other securement material or means. In some embodiments, such as the embodiment illustrated in FIG. 6, four strain gauges are implemented with one pair of strain gauges 146-2, 146-3 being aligned in parallel near the center 148 of bottom wall 124 and the other pair of strain gauges 146-1, 146-4 are disposed in parallel with one another adjacent to one another and perpendicular to gauges 146-2, 146-3. Put another way, parallel gauges 146-1 and 146-4 are disposed farther way from center 148 than gauges 146-2 and 146-3, which are disposed perpendicular to gauges 146-1 and 146-4.

The center 148 of diaphragm 124 experiences a higher tangential strain compared to the outer edge 140, which experiences a higher radial strain of opposite polarity. The particular placement of these gauges 146 on so-called "axes of neutrality," which refer to regions 150-1, 150-2 on diaphragm 124 where compression and tension are close to zero. Such minimization of net forces is created by extending the angle or ridge 140. This technique is designed to minimize mechanical deformations in the affixing substance. Such placement of gauges 146 increases the stability and lifespan of the gauges 146 as the strain and resulting deformation experienced by the epoxy affixing gauges 146 to diaphragm 124 is minimized.

For example, potential drift of resistive-based pressure sensors comes from a number of sources that alter the physical properties of the gauge 146, which causes net electrical characteristics of the gauge elements 146, e.g., resistance, to change in an unpredictable fashion. These sources include deterioration of the gauges, warping or fatigue of the sensor, and a gradual breakdown of the adhesive used to attach the gauges to the sensor. An extended ridge diaphragm advantageously allows for the ends of the semiconductor strain gauges 146 to be placed along two neutral axes where zero strain, or close to zero strain, is experienced. A neutral axis arises at transition point from compressive to tensile stress as shown in FIG. 6. By extending a peripheral ridge 140 upon the outside edge of the diaphragm 124 (approximately ⅒th the radius of the diaphragm), the diaphragm 124 effectively includes two neutral axes where strain is negligible as shown in the lower portion of FIG. 6. Placing the ends of the semiconductor gauges 146 along the two neutral axes provides enhanced stability and durability.

In some embodiments, the two radial strain gauges 146-1, 146-4 are oriented 90 degrees from each other instead of 180 degrees as illustrated in FIG. 6. Such arrangement results in partial cancellation of forces induced on the sides of the diaphragm 124.

The thickness of the epoxy used to attach gauges 146 to diaphragm 124 can be minimized to reduce the amount of viscoelastic drift caused during normal usage, particularly when a constantly elevated pressure is exerted on the diaphragm as in the human body. To support the minimization of thickness of epoxy used, a silicon dioxide or other insulating layer is grown on the bottom of the strain gauges 146 or on inner surface 144 of diaphragm 124 such that the adhesive employed need not be thick enough to serve as the only insulating element.

In some embodiments, such as the embodiment illustrated in FIG. 2, strain gauges 146 are coupled to contact blocks 152, which may be disposed on interior surface 154 of side wall 126 of distal component 118. The coupling between strain gauges 146 and contact block 152 is provided by wires 156. Wires 156 also connect contact block 152 to PCB 114 as illustrated in FIG. 2. In some embodiments, contact block 152 is omitted and wires directly connect strain gauges 146 to PCB 114.

Figure 7:
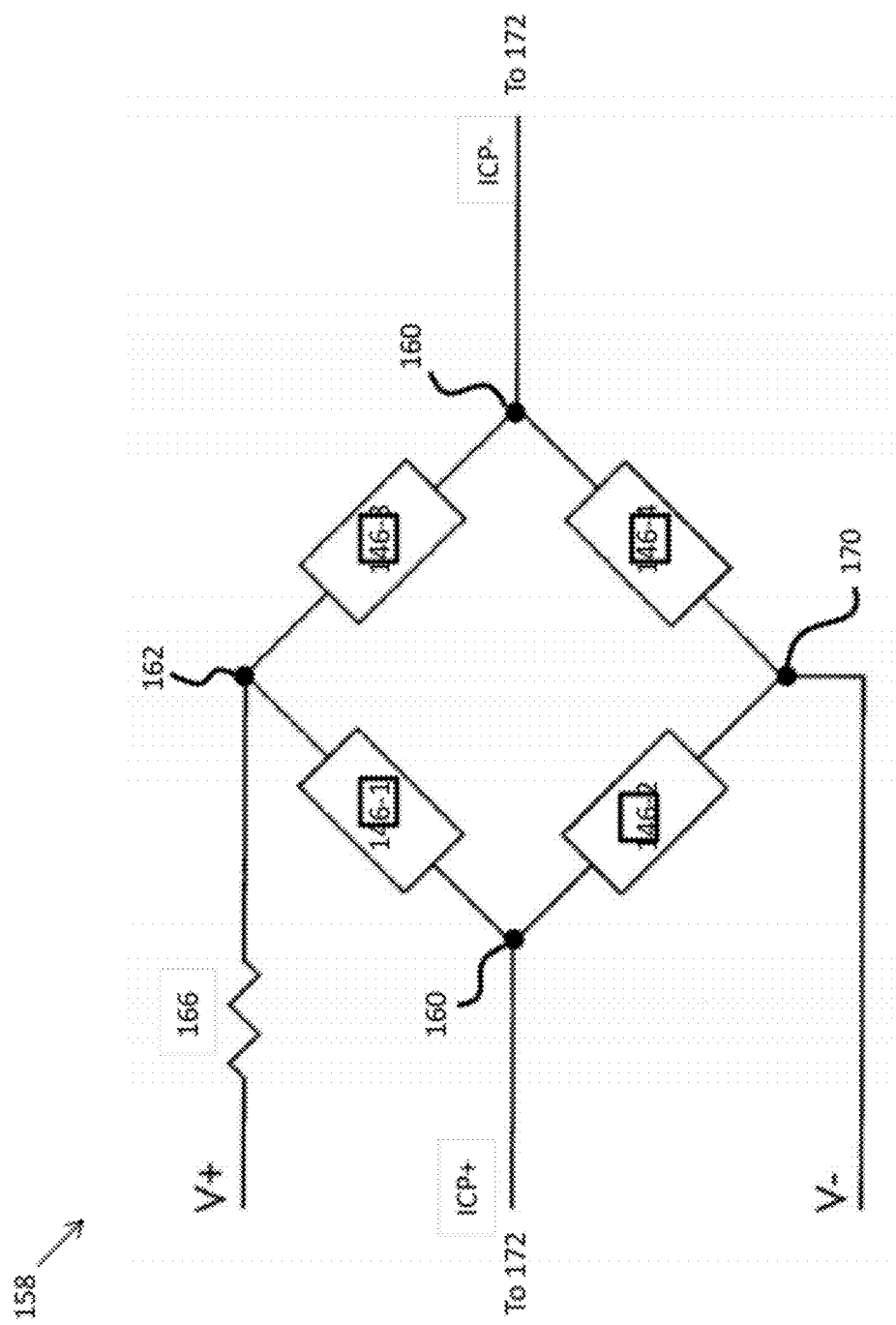
FIG. 7 illustrates one example of the electrical connections of the sensors illustrated in FIG. 6.

Strain gauges 146 are electrically connected to form a full Wheatstone bridge 158 as illustrated in FIG. 7. In particular, strain gauge 146-1 is coupled to strain gauge 146-2 at node 160, which serves as a first output node of Wheatstone bridge 158. Strain gauge 146-1 is also coupled to strain gauge 146-3 at node 162, which receives a positive voltage from a first voltage source 164 through resistor 166. Strain gauge 146-3 is coupled to strain gauge 146-4 at node 168, which serves as a second output node for Wheatstone bridge 158. Strain gauges 146-4 and 146-2 are coupled together at node 170, which is coupled to a low voltage power supply such as ground. However, one of ordinary skill in the art will understand that nodes 162 and 170 may be coupled to other supply voltages and that positive and negative do not necessarily have a physiological meaning in connection with ICP.

Figure 8:
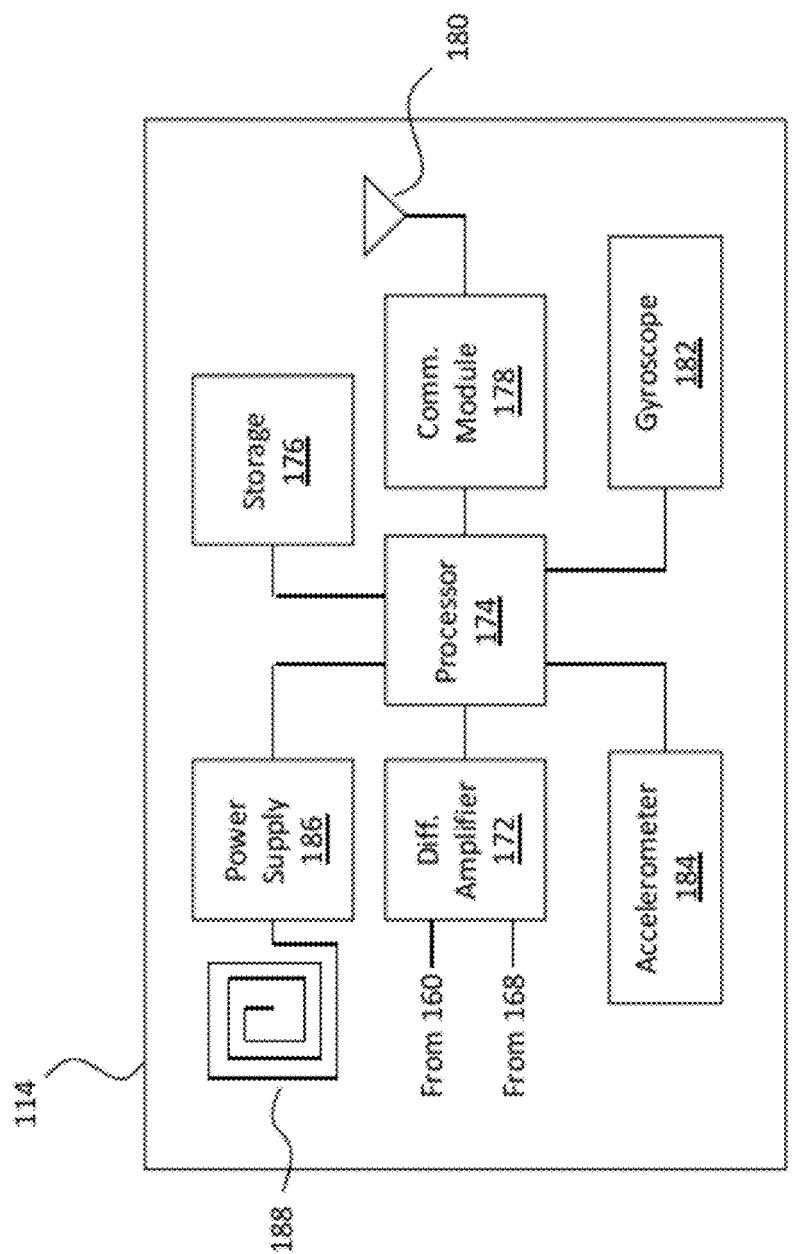
FIG. 8 illustrates one example of a printed circuit board and the circuitry disposed on the printed circuit board in accordance with the intracranial pressure monitoring device illustrated in FIG. 1.
Figure 9B:
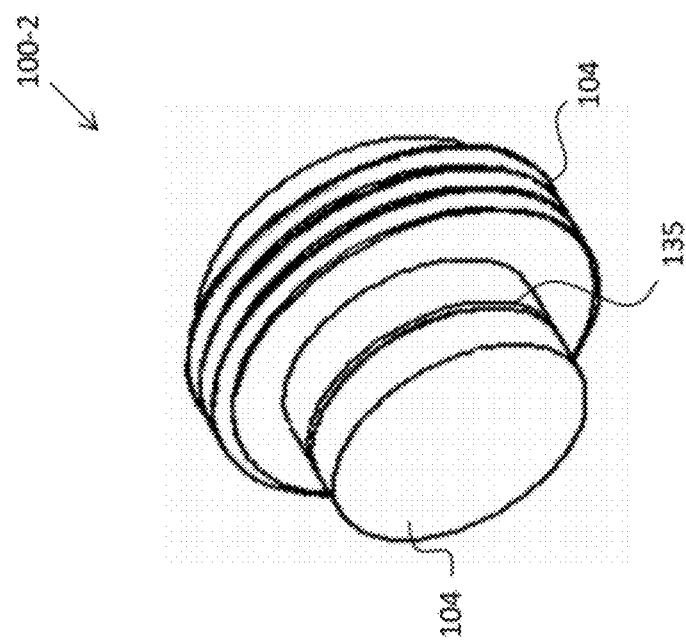
FIGS. 9A-9D are various views of another example of an intracranial pressure monitoring device.
Figure 9A:
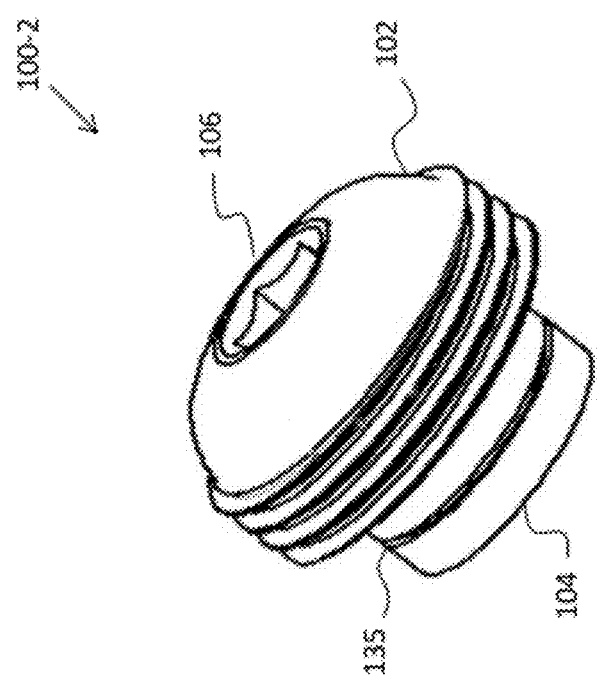
Figure 9D:
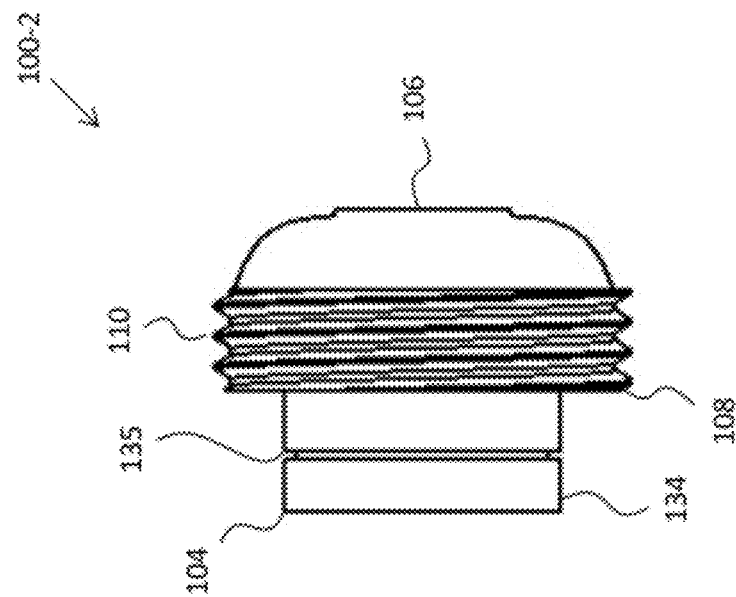
Figure 9C:
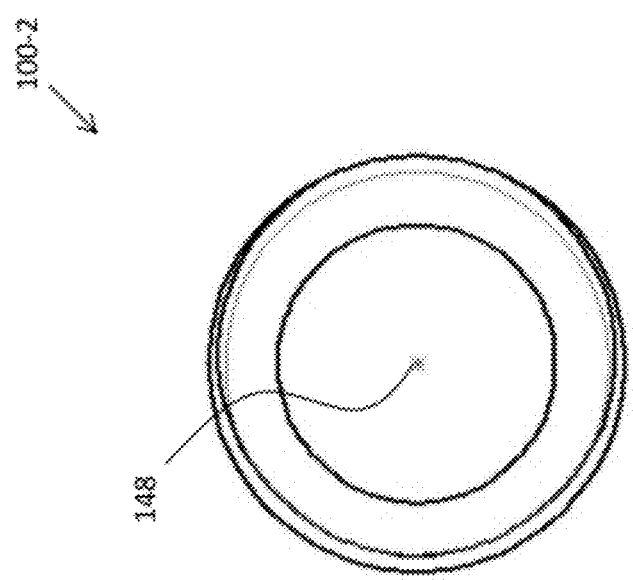

FIG. 8 illustrates some of the circuitry that may be formed on PCB 114. The circuitry formed on PCB 114 may include discrete components and/or be formed in an integrated circuit ("IC") or packaged together as an application specific integrated circuit ("ASIC"). As shown in FIG. 8, a low-drift differential amplifier 172 receives signals from nodes 160 and 168 of Wheatstone bridge 158 and outputs a signal to a microprocessor 174, which is configured with an analog-to-digital converter ("ADC"). In some embodiments, the ADC is a discrete component separated from microprocessor 174. Microprocessor 174 is in signal communication with a non-transient computer readable storage medium 176, such as a random access memory ("RAM"), a flash memory, or other storage device, and with a communication module 178 configured for radio frequency ("RF") communication or communication using other frequencies.

RF communication module 178 is coupled to an antenna 180 configured to transmit and receive wireless signals. In some embodiments, communication module 178 is configured to communicate using Bluetooth, Near-Field Communication, or other communication protocol for near or distant communication. In some embodiments, communication module 178 is a transceiver configured to transmit and receive signals in an unregulated band, such as the 2.4 GHz frequency band. One of ordinary skill in the art will understand that other communication protocols and transmission frequencies may be used.

Additional circuitry may also be disposed on PCB 114 for enhanced data gathering. In some embodiments, for example, a gyroscope 182, an accelerometer 184, both, or another device for determining an orientation of ICP monitoring device 100 relative to a vertical direction or axis are disposed on PCB 114. The gyroscope and/or accelerometer may be single- or multi-axis devices manufactured using MEMS technology. These devices 182, 184 are utilized to determine the orientation of the patient's head, which affects the measured ICP as will be understood by one of ordinary skill in the art. For example, a patient's ICP will be higher when supine, e.g., perpendicular to the vertical direction or axis, than when sitting upright (e.g., parallel to the vertical direction or axis), due to the effect of gravity on the patient's cerebral spinal fluid ("CSF").

In some embodiments, gyroscope 182 and/or accelerometer 184 are configured for use in long-term sensor implantation scenarios to monitor a patient's orientation. For example, devices 182 and 184 can be used to detect a patient falling and cause microprocessor 174 to record the time of the fall for later correlation with a rise in ICP. In some embodiments, the detection of a fall will trigger an alert to the patient, primary caregiver, or emergency services based on a rise in ICP associated with a fall. Patient orientation is also useful in determining and recording when the patient is awake or asleep. For example, diagnostic measurements for normal pressure hydrocephalus are typically obtained when a patient is sleeping. Microprocessor 174 can be programmed to obtain such measurements when gyroscope 182 and/or accelerometer 184 provide signals to microprocessor 184 identifying that the patient is lying down. In some embodiments, such measurements are only recorded after it is determined the patient has been lying down for a period of time that exceeds a threshold, e.g., 10 minutes, 20 minutes, etc.

The electronics disposed on one or more PCBs 114 are powered by a power supply 186. In some embodiments, power supply 186 includes a battery while in other embodiments the electronics are powered by another power supply. For example, the electronics disposed on PCB 114 can receive power via inductive coupling between a coil antenna 188 in or on top of the implant and another coil antenna in or outside of an external unit as described in greater detail below. Each of these coil antennas make up a portion of a resonant circuit that includes inductors, capacitors, and resistors such that the circuit is electrically resonant at a predetermined frequency. A powered resonant circuit brought into the vicinity of a circuit resonant at a close frequency or a harmonic will inductively couple with the second circuit thereby inducing a current to flow. This current can be used to run the implanted electronics or charge a capacitor of power supply 186 that stores energy for powering the electronics disposed on PCB 114.

Another embodiment of an improved ICP monitoring device 100-2 illustrated in FIGS. 8A-8D, which provide various views of device 100-2. As illustrated in FIGS. 8A-8D, ICP monitoring device 100-2 includes a housing 102 extending from a distal end 104 to a proximal end 106. In some embodiments, housing 102 has a circular cross-sectional area as best seen in FIGS. 8C and 8D and is formed from a metal such as, for example, titanium, stainless steel, gold, silver, or other biocompatible metal.

As best seen in FIGS. 8A, 8B, and 8D, the exterior surface 108 of proximal portion 116 of housing 102 includes self-tapping threads 110 for securing ICP monitoring device 100-2 to the skull of a patient. Distal portion 118 of housing 102 includes a smooth outer surface 134 having an outer diameter that is smaller than an outer diameter of proximal portion 116 enabling distal portion 118 to pass through the inner dimension of the ridge of bone created by an anti-plunge cranial perforator as will be understood by one of ordinary skill in the art. In some embodiments, housing 102 and the burr hole created by such drilling mechanism are complementary such that CSF is prevented from leaking through the burr hole around housing 102.

In some embodiments, a circumferential trough 135 is formed along the length of distal portion 118 as can be seen in FIGS. 8A, 8B, and 8D. Trough 135 advantageously isolates fixed-edge extended-ridge diaphragm 124 and strain gauges 146 from stresses and strains afflicted on the housing during implantation. Such stresses and strains can deform diaphragm 124 and cause damage or measurement drift.

Figure 10:
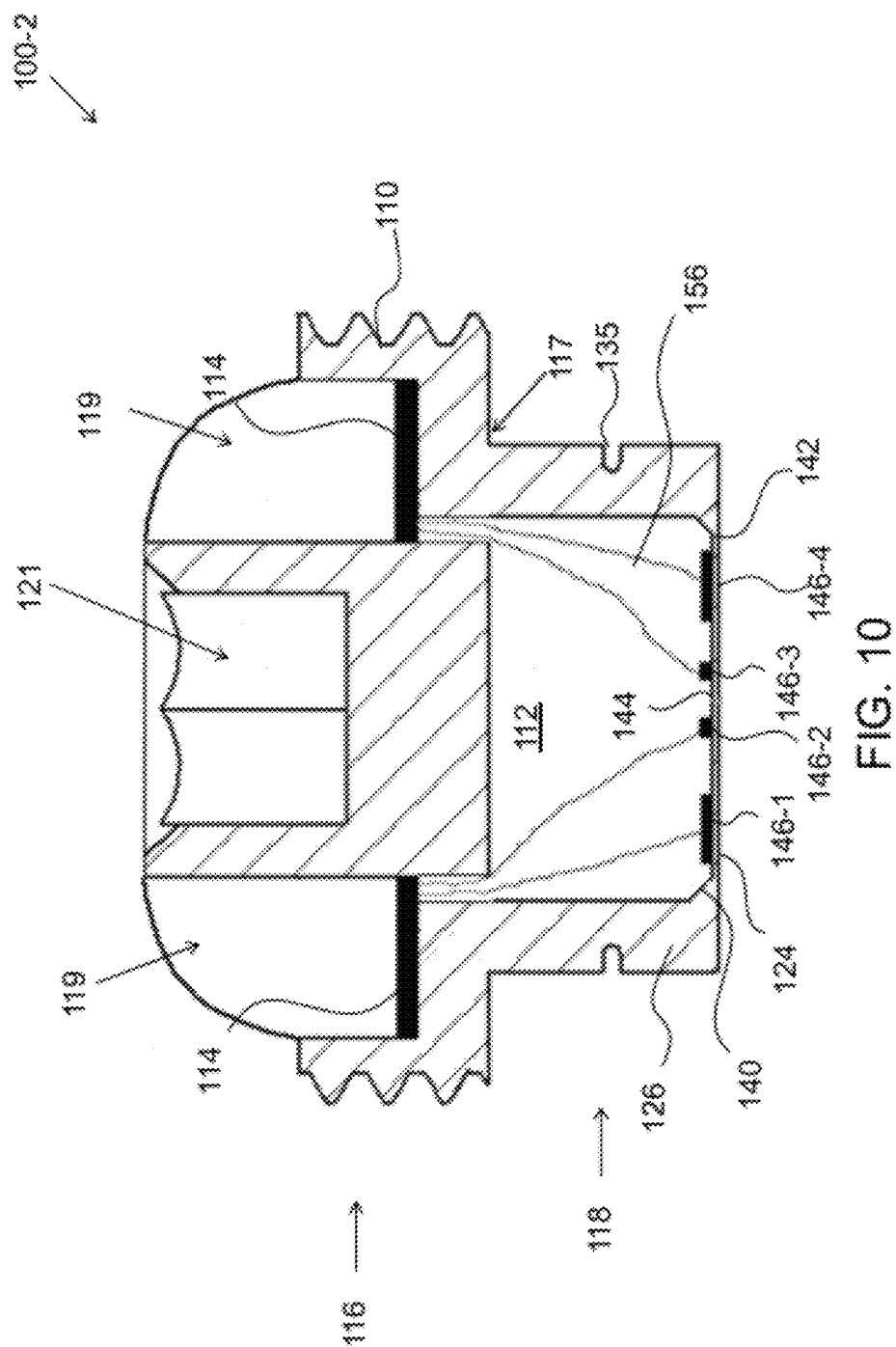
FIG. 10 is a cross-sectional view of the intracranial pressure monitoring device illustrated in FIGS. 9A-9D.

Turning now to FIG. 10, it can be seen that distal portion 118 of housing 102 defines an internal chamber 112 in which strain gauges 146-1, 146-2, 146-3, and 146-4 are disposed. As described above, strain gauges 146 are affixed to bottom wall 124, which forms the fixed-edge diaphragm, by epoxy or other means. As described above with respect to FIG. 6, strain gauges 146 can be disposed on bottom wall 124 such that strain gauges 146-2, 146-3 are aligned in parallel with one another near the center of bottom wall 124 and the other pair of strain gauges 146-1, 146-4 are disposed in parallel with one another adjacent to one another and perpendicular to gauges 146-2, 146-3. Extended ridge 140 extends at a non-perpendicular angle with respect to side wall 126 and bottom wall 124 to change the stress concentrations as described above.

The thickness of the epoxy used to attach gauges 146 to diaphragm 124 can be minimized to reduce the amount of viscoelastic drift due to long-term variations in average pressure, due to, for example, a patient traveling to a higher or lower altitude. To support the minimization of thickness of epoxy used, a silicon dioxide or other insulating layer is grown on the bottom of the strain gauges 146 or on inner surface 144 of diaphragm 124 such that the adhesive employed need not be thick enough to serve as the only insulating element. Side wall 126 extends from bottom wall 124 to interface 117 where distal portion 118 is joined to proximal portion 116.

Proximal portion 116 defines a recessed area 119 that houses PCB 114 on which the electronics are disposed. Silicon potting or other biocompatible material disposed in recessed area 119 over PCB 114 and the electronics disposed thereon. The shape formed by the potting is designed to minimize the potential for skin necrosis around the implant's external proximal end. Placing PCB 114 and the electronics in recessed area 119 reduces the interference of the housing material on the function of the electronics, particularly the coil antenna.

Proximal portion 116 also defines an engagement feature 121 that is configured to receive or engage a tool for aiding in insertion of ICP monitoring device 100-2 into a skull of a patient. In some embodiments, engagement feature 121 is configured to receive a tool having a hexagonal cross-sectional area, although one of ordinary skill in the art will understand that engagement feature 121 may be complementary to tools having other cross-sectional geometries including, but not limited to, stars and squares.

In some embodiments, proximal portion 116 and distal portion 118 are formed from a single piece of a rod. In some embodiments, proximal portion 116 and distal portion 118 are coupled together at interface 117 by laser welding or screw threads. In some embodiments, a ceramic feed-through is brazed to side wall 126 and to proximal portion 116 to join proximal portion 116 to distal portion 118 at interface 117 and to allow wires 156 to pass from chamber 112 defined by distal portion 118 to recessed area 119 defined by proximal portion 116.

Proximal portion 116 and distal portion 118 are coupled together to provide a hermetic seal such that chamber 112 has a known internal pressure. As described above, chamber 112 can be filled during manufacturing with a gas such as Argon, Helium, or other combination of gases. In some embodiments, chamber 112 is filled with an electrically insulating liquid or is evacuated prior to sealing. The effect of controlling the contents of the sealed chamber 112 is to create a reference pressure against which the degree of deformation of the fixed-edge diaphragm may be measured in order to correlate to an external pressure experienced by the diaphragm 124. As described above, controlling the contents of sealed chamber 112 also controls and defines the characteristic pressure changes in the chamber contents, which affects the gauges and pressure readings as the temperature changes.

In some embodiments, the external surface 142 of bottom wall 124, which forms the diaphragm, is electro-polished or coated with materials or drugs known to prevent scar tissue overgrowth. Fibrous tissue overgrowth occurs within several weeks of implantation of foreign material into the body. Examples of materials that may be deposited on external surface 142 include, but are not limited to, polyvinylpyrrolidone ("PVP"), phosphoryl colene, polyethylene oxide ("PEO"), hydro-gels, and paralene, to name a few possible materials. Examples of drugs that may be disposed on the external surface 142 of bottom wall 124 includes, but are not limited to, anti-inflammatory agents, cell cycle inhibitors, anti-platelet agents, anti-thrombin compounds, and thrombolytic agents.

External surface 142 is fabricated to provide a surface that is as flat as possible. As described above, a flatter diaphragm 124 is less compliant and thus the electrical changes induced in gauges 146 mounted on the diaphragm 124 will have a higher gain than from a less flat diaphragm. Thus, a flat diaphragm minimizes the dampening effects of tissue overgrowth by enabling more sensitive gauge measurements.

Figure 11:
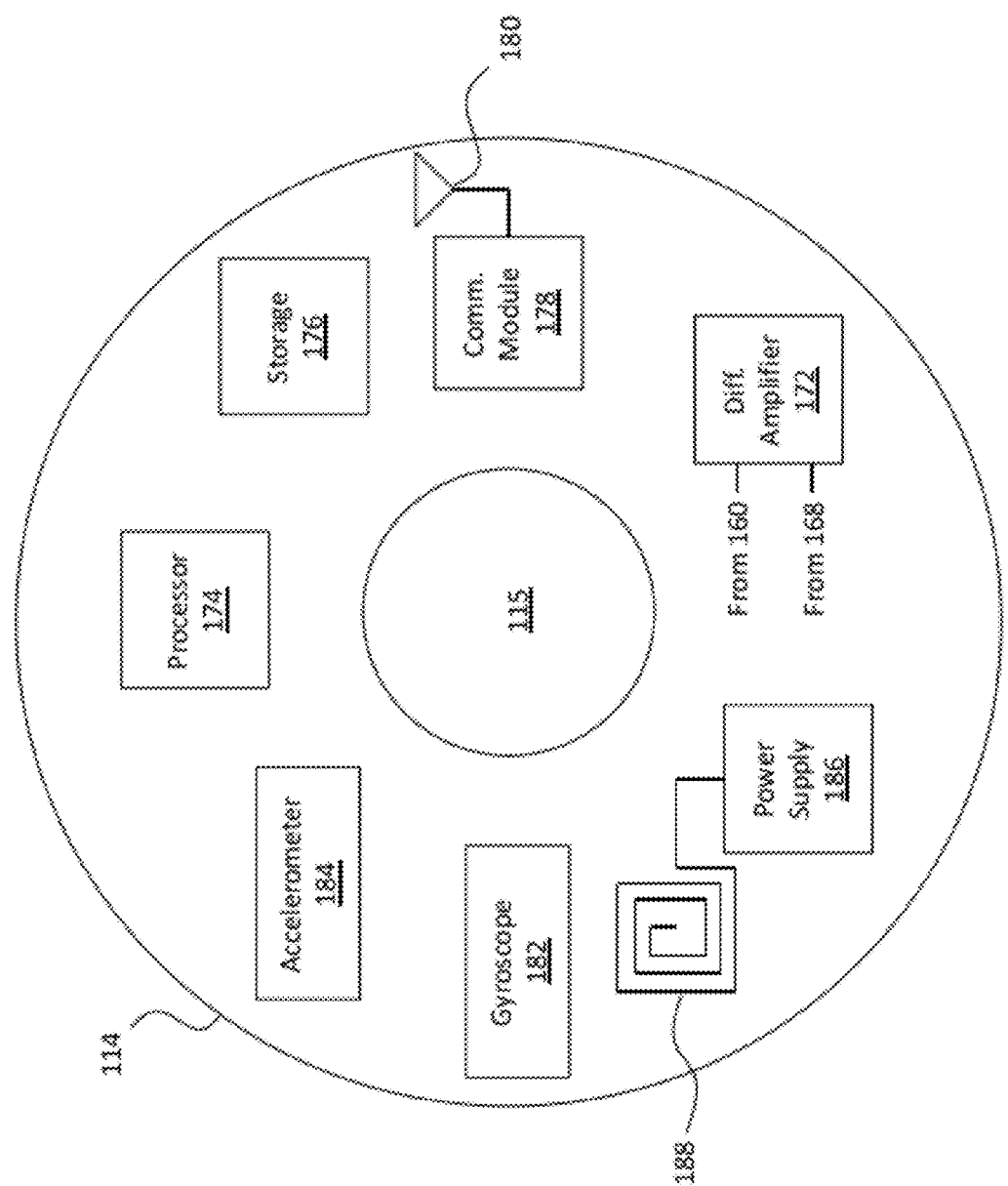
FIG. 11 illustrates one example of a circular printed circuit board and the circuitry disposed on the circular printed circuit board in accordance with the intracranial pressure monitoring device illustrated in FIGS. 9A-9D.

Strain gauges 146 are coupled to PCB 114 via wires 156 and are electrically connected to form a full Wheatstone bridge 158 as illustrated in FIG. 7. FIG. 11 illustrates one example of a circular PCB 114 having a circular cutout 115. PCB is sized and configured to be received within recess 119 on which circuitry is formed. Locating PCB 114 in recess 119 isolates the electronics disposed on PCB 114 from chamber 112 to mitigate the effects of the housing 102 on the inductive coupling between housing 102, antenna 180, and coil 188.

As shown in FIG. 11, a low-drift differential amplifier 172 receives signals from nodes 160 and 168 of Wheatstone bridge 158 and outputs a signal to a microprocessor 174, which is configured with an ADC. Microprocessor 174 is in signal communication with a non-transient computer readable storage medium 176, such as a RAM, a flash memory, or other storage device, and with a communication module 178 configured for wireless communication. Other circuitry for performing analog/digital filtering, analog/digital smoothing, frequency analysis, and time domain operations can be disposed on PCB 114.

RF communication module 178 is coupled to an antenna 180 configured to transmit and receive wireless signals. In some embodiments, communication module 178 is configured to communicate using Bluetooth, Near-Field Communication, or other communication protocol for near or distant communication. In some embodiments, communication module 178 is a transceiver configured to transmit and receive signals in an unregulated band, such as the 2.4 GHz frequency band. One of ordinary skill in the art will understand that other communication protocols and transmission frequencies may be used.

A gyroscope 182 and/or an accelerometer 184 are disposed on PCB 114. The gyroscope and/or accelerometer may be single- or multi-axis devices manufactured using MEMS technology. These devices 182, 184 are utilized to determine the orientation of the patient's head, which affects the measured ICP as will be understood by one of ordinary skill in the art. For example, a patient's ICP will be higher when supine than when sitting upright or standing upright, due to the effect of gravity on the patient's CSF.

Additionally, gyroscope 182 and/or accelerometer 184 disposed on PCB 114 may be utilized to determine and/or identify medically relevant events such as, for example, a patient falling. Devices 182, 184 can be used to record the force with which the fall impacted the patient's skull and be correlated with changes in ICP before, during, and/or after the event to determine various causes and effects of the event as well as aid in medical diagnosis and/or treatment.

Figure 12A:
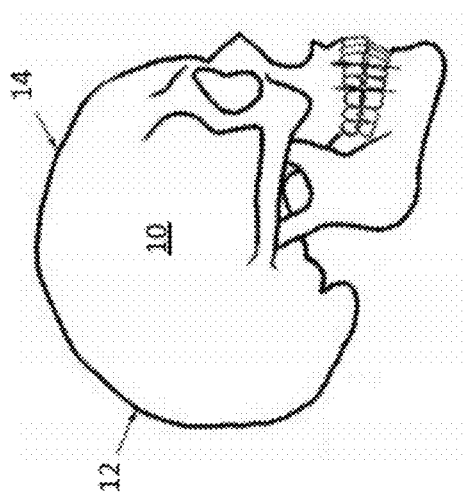
FIG. 12 illustrates various places on a human skull at which the intracranial pressure monitoring devices may be positioned.

The improved ICP monitoring devices 100-1, 100-2 ("ICP monitoring devices 100") described above may be installed at various locations in the skull 10 of a patient. In some embodiments, an ICP monitoring device 100 is installed at Frazier's Point 12 or in Kocher's Point 14 in a skull as illustrated in FIG. 12A. The method of installing an ICP monitoring device 100 in a skull 10 of a patient is described with reference to FIGS. 12A and 12B.

Figure 12B:
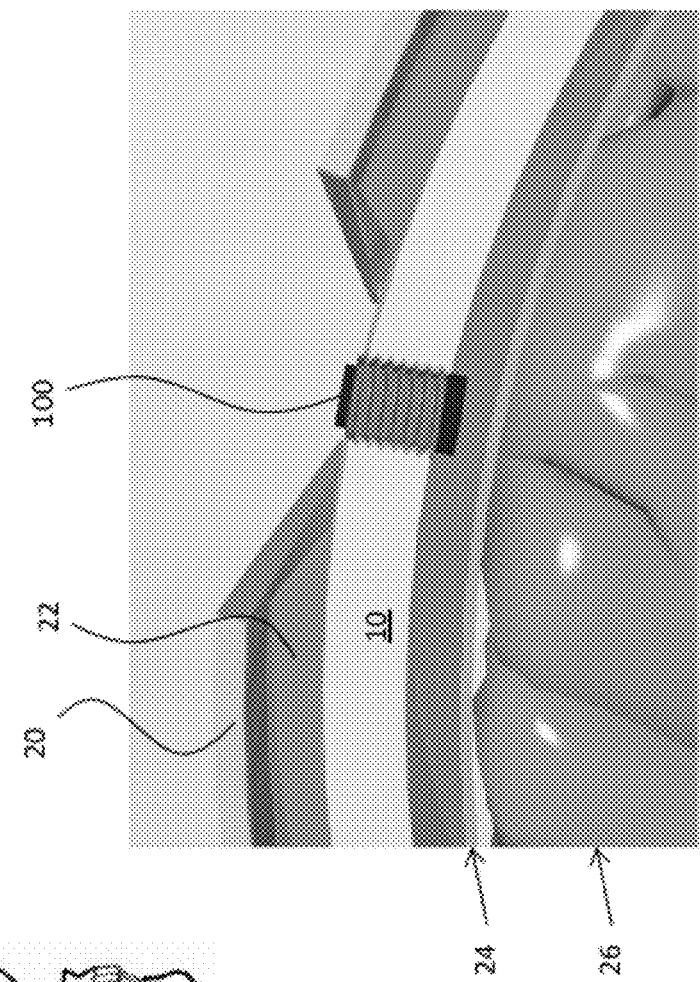

The skin 20 and fascia 22 are removed from the insertion side to expose the patient's skull 10 as best seen in FIG. 12B. As described above, the insertion site may be at the Frazier's Point 12 located 3 cm lateral to the midline and 6 cm superior to the inion, the Kocher's Point 14 located 11 cm posterior to the nasion and 2.5 cm lateral to midline, or at another location as will be understood by one of ordinary skill in the art. For example, ICP monitoring device 100 both above or below the tentorium at locations commonly used positions for placement of intraventricular catheters.

A cranial burr hole is made in a patient's skull 10 by a surgeon using an anti-plunge cranial perforator, a drill, or other tool. The hole is made by the surgeon to expose the dural sac 24 surrounding the brain 26 of the patient.

An ICP monitoring device 100 is then inserted into the hole formed in the skull 10 as illustrated in FIG. 12B. In some embodiments, housing 102 is threaded into skull bone 10 such that self-tapping threads 110 dig into skull bone 10 as ICP monitoring device 100 is rotated. In embodiments when the cranial burr hole has an irregular shape, e.g., non-circular shape, an adapter grommet (not shown) defining a central passageway sized and configured to receive ICP monitoring device 100 is first inserted to cranial burr hole. The adapter grommet may have a cross-sectional area that is complementary to the cranial burr hole formed in the patient's skull 10.

In some embodiments in which housing 102 does not include threads 110, i.e., the outer surface 108 of housing is smooth, proximal portion 116 may have an outer diameter that is greater than a diameter of cranial burr hole such that distal portion 118 is received within the hole and proximal portion 116 abuts the outer surface of skull bone 10. Tabs 103 (FIG. 5) may outwardly extend from proximal portion 116 and each define an opening 105 sized and configured to receive screws that assist in affixing ICP monitoring device 100 to skull 10.

The depth to which ICP monitoring device 100 is installed may be varied. For example, ICP monitoring device 100 is installed such that diaphragm 124 is disposed flush with or slightly below the inner table of the skull such that diaphragm 124 contacts dura 24.

In some embodiments, diaphragm 124 is positioned below a fenestrated dural layer such that diaphragm 124 is in contact with the pial layer or brain parenchyma tissue. Such positioning may provide for improved sensitivity to monitoring as well as reducing and/or eliminating impedance due to the dura matter. A surgeon may be notified that ICP monitoring device is properly positioned by device 100 generating a signal from gauges 146 in response to diaphragm 124 contacting dura 24. The signal may be received by an external unit (described below), which signals the surgeon installing monitoring device 100 by emitting an audio and/or visual indication.

Monitoring device 100 can also collect data during the installation process concerning stress and strain on side wall 126. For example, strain gauges 146 can generate signals identifying detected strain on housing 124 while the ICP monitoring device 100 is being twisted into skull 10. In such a configuration, ICP monitoring device 100 can alert the surgeon if excessive strain is detected. Excessive strain during implantation may be a marker of improper implantation and may lead to inaccurate pressure readings due to diaphragm deformation.

Figure 19:
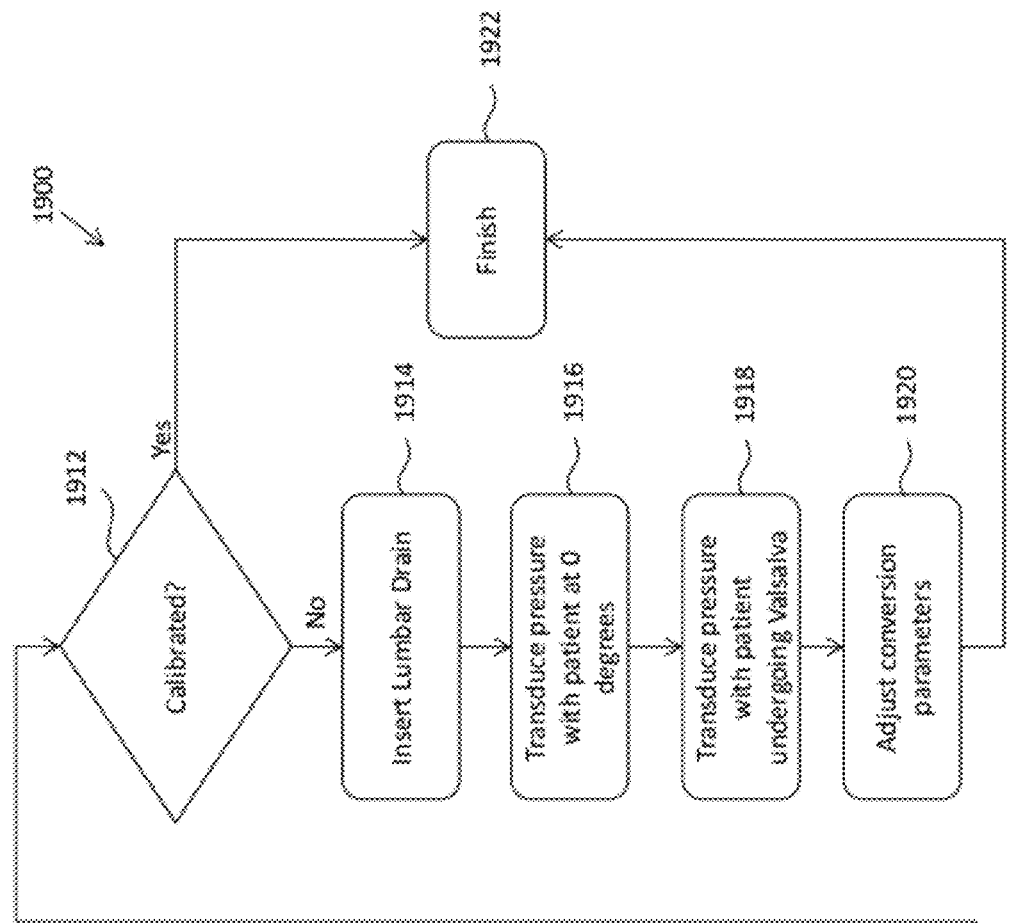
FIG. 19 is a flow diagram of one example of a method of calibrating an ICP monitoring device in accordance with some embodiments.

Once the ICP monitoring device 100 is installed, initial measures can be used to calibrate the device as will be described with reference to FIG. 19. As shown in FIG. 19, an ICP monitoring device 100 is implanted in a patient at block 1902. At block 1904, a pressure reading is taken and assessed to determine the quality of the contact of ICP monitoring device 100 and the intracranial pressure region. The pressure reading taken by ICP monitoring device 100 may be transmitted to an external device, such as an external device 300, 400, 500 described in greater detail below, such that a user may be able to assess the quality of the implant.

At block 1906, a decision is made as to whether ICP monitoring device 100 has been properly implanted. In some embodiments, an external device may display a graphical representation of an ICP waveform to a user on a display such that the user may assess whether or not the ICP monitoring device is properly implanted. In some embodiments, ICP monitoring device is placed in a mode in which it assesses the pressure signals to determine whether implantation has been properly made. For example, processor 174 of ICP monitoring device receives the sensed signals from strain gauges 146 and determine a peak-to-peak signal voltage to determine whether sufficient contact has been made between diaphragm 124 and the intracranial surface of a patient. If it is determined that implantation was not successful, e.g., the contact between diaphragm 124 and the intracranial pressure surface of a patient is not sufficient to detect pressure accurately, then the implantation procedure at block 1902 is performed again.

If it is determined that sufficient contact has been made between diaphragm 124 of ICP monitoring device 100 and an intracranial surface of a patient, then method 1900 proceeds to block 1908 where a plurality of calibration readings are recorded at different elevations. For example, the patient can be positioned in a supine position with their head flat, which may be recorded as a zero degree elevation. In such a position, ICP monitoring device 100 stores the pressure waveform for a predetermined period of time as well as a position measurement that corresponds to signals received from gyroscope 182 and/or accelerometer 184. Subsequently, the patient can be elevated to 30 degrees, 60 degrees, 90 degrees, and other positions and ICP monitor 100 can record the pressure waveform for the predetermined period of time along with the values measured by gyroscope 182 and/or accelerometer 184 associated with this position.

Alternatively or additionally, the patient can be positioned in a completely upright, or standing, position and ICP monitoring device 100 can record the waveforms received from strain gauges 146 along with the values measured by gyroscope 182 in these positions. As will be understood by one of ordinary skill in the art, processor 174 may read values from gyroscope 182 and store the values in non-transient computer readable storage 176.

At block 1910, ICP values are calculated for each of the different positions at which the patient was positioned. The ICP values are calculated based on the stored waveforms and are recorded with the position data.

At decision block 1912, the calculated ICP value is compared to a measured ICP value to determine if ICP monitoring device has been calibrated. For example, if the calculated ICP value is not equal to the measured ICP value, then ICP monitoring device 100 is not calibrated. If the ICP value is equal to the measured ICP value, then ICP monitoring device 100 is calibrated and method 1900 is finished at block 1922.

If ICP monitoring device 100 is not calibrated, then method 1900 proceeds to block 1914 where a lumbar drain is inserted into patient. As will be understood by one of ordinary skill in the art, a lumbar drain is typically a flexible, soft plastic tube that is inserted into the lower back of a patient to remove CSF. The tube can be coupled to a drainage bag for capturing the removed CSF.

At block 1916, the pressure is transduced with a patient in a zero degree position. The lumbar drain is coupled to a pressure transducer that is calibrated to zero at the level of the patient's tragus, which is used as the common reference point by physicians for ICP monitoring.

At block 1918, the pressure is transduced with a patient undergoing a Valsalva maneuver. The Valsalva maneuver can be performed in various ways. One way is to have the patient close his/her airway, e.g., closing his/her mouth and pinching his/her nose closed, and trying to exhale to increase intrathoracic pressure. In this method, the patient can exhale against a pressure recording device such as a manometer, which can record the intrathoracic pressure. Another way to induce a Valsalva is to have the patient bear down as if having a bowel movement. The Valsalva maneuver increases intrathoracic pressure, thereby decreasing venous outflow from the brain and increasing intracranial pressure. Performing Valsalva maneuvers while the patient is supine allows for measurement of a range of intracranial pressures and waveforms with each Valsalva.

At block 1920, conversion parameters are adjusted based on the recalibration procedures performed at blocks 1916 and 1918. Such adjustable parameters include, but are not limited to, the raw voltage reading of the Wheatstone bridge 158 when the patient is at various elevations, a calculated line or curve of best fit between various Wheatstone bridge voltage readings, the raw voltage reading of the gyroscope 182 or accelerometer 184 at various elevations (to account for, e.g., implantation that is not perfectly level), and various calculated waveform parameters at various patient elevations as described below. Once the adjustments have been made and ICP monitoring device 100 is calibrated, method 1900 moves to block 1922 and the calibration is concluded.

Recording the measured values when the patient is disposed in known positions provides ICP monitoring device 100 with the ability to minimize the drift of gyroscope readings and maximizing the accuracy of patient position estimation, which leads to improved internal pressure measurements and calibration. Although calibration method 1900 is described as being performed when ICP monitoring device has been implanted, one of ordinary skill in the art will understand that the calibration can be conducted while the sensing diaphragm is exposed to air prior to implantation or when ICP monitoring device 100 is disposed within a shallow depth of fluid.

The calibrated ICP monitoring device 100 is configured to sense and store data concerning intracranial pressure as detected by strain gauges 146. As will be understood by one of ordinary skill in a measure of pressure can be derived from a computed correlative relationship between sensor-measured pressure and a number of waveform features. A correlative relationship can include any relationship, such as a formula, a graph, a curve, a linear relationship, a non-linear relationship, a neural network, a classifier, or any other relationship that provides a value of one variable when presented with a value of another variable or variables.

Figure 20:
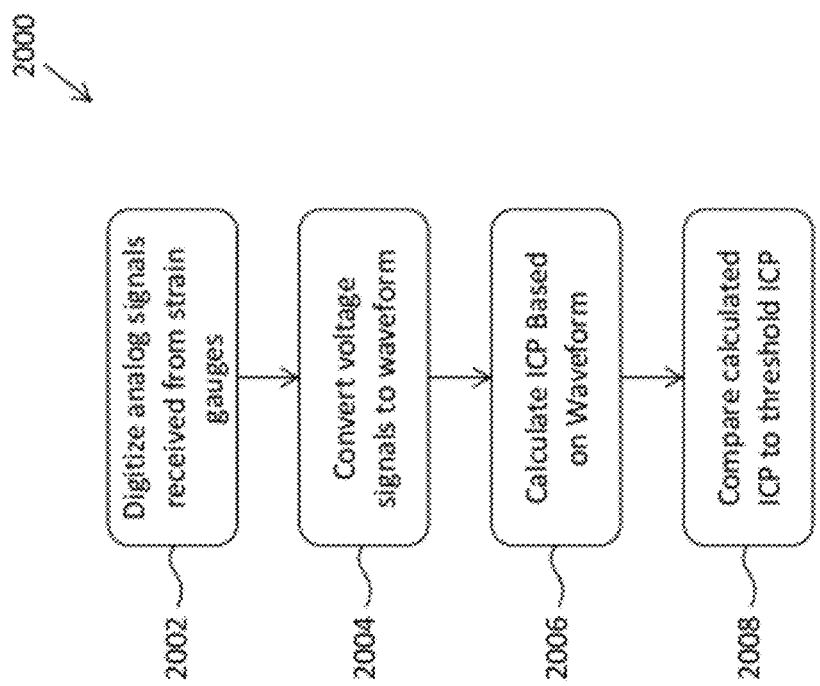
FIG. 20 is a flow diagram of one example of monitoring performed by an ICP monitoring device in accordance with some embodiments.

The processing of the signals received from strain gauges 124 is described with reference to FIG. 20. Mechanical strains on diaphragm 124 are sensed by strain gauges 146, which generate electrical analog signals in response. These analog signals are digitized at block 2002 by an ADC, such as an ADC of processor 174 or a separate ADC.

At block 2004, the digitized voltage are processed to generate an ICP waveform, such as the ICP waveform illustrated in FIG. 13. In some embodiments, the digitized voltages are converted to a characterized waveform in a fixed method, and in some embodiments, the digitized voltages are converted to a characterized waveform in a dynamic method as will be understood by one of ordinary skill in the art. As shown in FIG. 13, the ICP waveform includes three peaks (P1, P2, P3).

At block 2006, an ICP value is calculated based on the waveform using a linear, quadratic, or other approximation method. The values derived from the waveform features can be selected from a group of parameters for each peak including amplitude, rate of ascent, and rate of descent, among others. Additionally, timing of any of the aforementioned waveform features can be taken with respect to the cardiac or respiratory cycle or timing of another ICP waveform feature. A phase shift can also be calculated between the waveform of both the intracranial pressure and blood pressure waveforms which also serve as an index of intracranial pressure, intracranial compliance, or another physiological parameter.

Processor 174 can be configured to identify initial waveform feature indices and correlations between these indices can be captured from various sensor modalities after implantation in a patient. Processor 174 can also be configured to compare current real-time waveform features to an initial set of reference calibration features established for the various sensor modalities enables the detection of either a physiological condition or an improper calibration of the ICP monitoring device.

A library of patient waveform data acquired from multiple patients and time points across a number of sensor modalities can be stored in non-transient computer storage 176. At block 2008, the measured waveforms are compared to waveforms in a waveform library stored in non-transient computer storage 176. Processor 174 determines whether there has been a change in a physiological condition of a patient, sensor baseline drift, or improper calibration of a sensor through this comparison. For example, if a difference between current real-time waveform and an ICP value stored in non-transient computer storage 176 corresponding to a same position is above a threshold value, then an error signal is generated notifying a patient or caretaker of a problem that there is a problem with the sensor. If a difference between the current real-time waveform and an ICP value stored in non-transient computer storage 176 corresponding to a same position is below a threshold value, then the data can be stored by ICP monitoring device 100 and/or transmitted to an external device 200, 300, 400, 500 for displaying the ICP measurement to a user.

Processor 174 is also configured to correlate measured pressures to changes in non-invasive measurements. Such measurements include, but are not limited to, carotid artery pressure waveforms, peripheral artery pressure waveforms, tonometry, MRI scanning algorithms, acoustic emissions, visual evoked potentials, transracial Dopplers, ultrasonic resonance, and skull pulsations. In one example, carotid artery pressure and peripheral artery pressure waveforms are used to analyze impedance changes in the carotid waveform attributable to intracranial impedance.

Other features such as the time delay between features, such as the systolic maximum and the dicrotic notch of a blood pressure waveform, are used by processor 174 to characterize intracranial impedance which can be correlated to measured pressure to determine actual pressure. Processor 174 is also configured to correlate or calibrate measured pressure against an invasive measurement of pressure such as pressure measured through a lumbar drain, an omaya reservoir, a ventricular catheter, cerebrospinal fluid shunt, or a vascular catheter in a vein or artery.

In some embodiments, processor 174 is configured to analyze a number of waveform features to provide information regarding the condition of the patient. Such conditions include, but are not limited to, a change in intracranial pressure, intracranial compliance, oxygenation, heart rate, temperature, respiratory rate, carotid pressure waveform, peripheral artery waveform, or in cerebral perfusion pressure. Algorithms utilizing a number of the waveform features or relations are stored in non-transient computer storage 176 for execution by processor 174. In some embodiments, the algorithms executed by processor 174 are used for the prediction of rises in ICP, diagnosis of acute stroke, tool for improved accuracy in diagnosis of normal pressure hydrocephalus, or assessing the responsiveness to a treatment aimed at changing intracranial compliance. Algorithms can include a number of mathematical functions or experimentally validated relationships, heuristic algorithms, transfer functions, statistical models, or deterministic models.

The waveform analyses described above may be performed by a processor separate from processor 174 after the data acquired by ICP monitoring device 100 is transmitted to an external unit. For example, the electronics of ICP monitoring device 100 are configured to permit bidirectional transmission of data such that data may be received from and transmitted to an external device.

In some embodiments, for example, data is transmitted from ICP monitoring device 100 to a separate device via an inductive coupling link. Data is sent by modulating a property of a resonant circuit, which may be coupled to or included in communication module 178 and/or antenna 180, in such a way so as to induce a detectable current change on the other end of the inductive coupling link. The modulation may be such that data transmitted is frequency shifted, phase shifted, etc. The circuitry connected to the resonant circuit is designed to filter out the carrier frequency at which the inductive coupling resonates, leaving just the data waveform, which may be decoded by digital electronics and interpreted in embedded software as will be understood by one of ordinary skill in the art.

In some embodiments, antenna 180 may be a separate antenna from inductive coupling link, which, when matched with appropriate circuitry, enables ICP monitoring device 100 to transmit data as will be understood by one of ordinary skill in the art.

An external unit can send commands over the inductive coupling link or separate antenna to the implanted electronics to program or select in which of several modes the processor 174 is to operate. Examples of such operating states include, but are not limited to, reprogramming, calibrating, streaming data for a predetermined amount of time, and long-term standalone operation.

A long-term, standalone monitoring operation is an operation in which the external device or unit is to be removed and ICP monitoring device 100 continues to record or sense ICP data. In such an operating mode, the circuit elements disposed on PCB 114 operate in a state of minimal power draw, which uses a low-power timing circuit to alternate between powering off and powering on some subset of the modules in the electronics. For example, processor 174 may periodically receive sensed signals from strain gauges 146 and store the data in storage 176. When not acquiring data, processor 174 may turn off one or more of gyroscope 182, accelerometer 184, communication module 178, ADC, on-board electronic components including electronic timers or clock modules, and other integrated circuits as will be understood by one of ordinary skill in the art. The recorded data can be transmitted to an external unit in response to receiving a trigger signal from the external unit or at a preprogrammed time.

Figure 14:
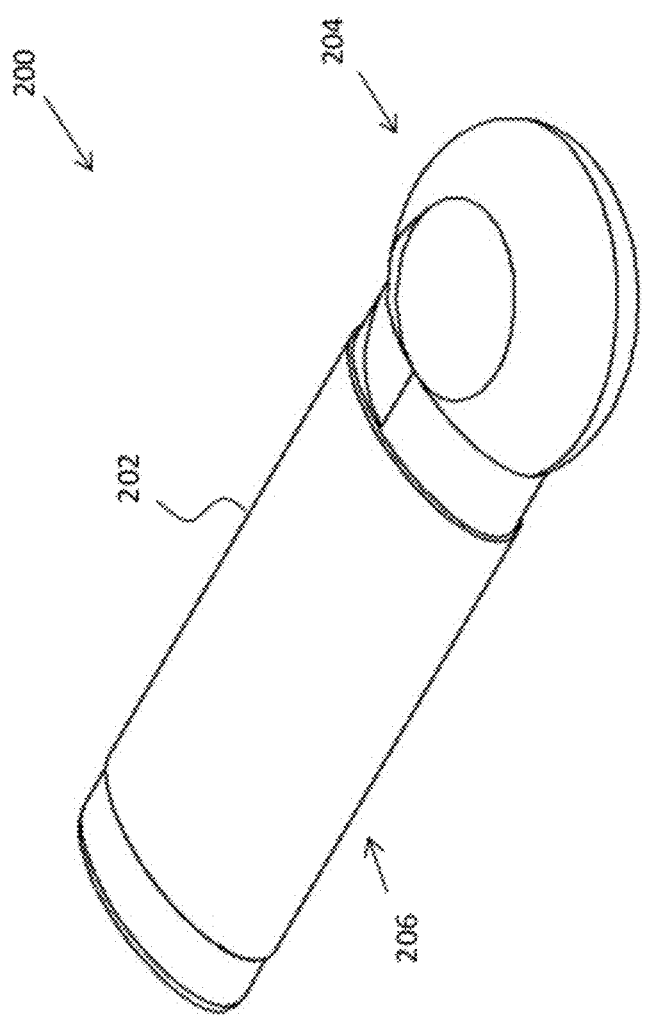
FIG. 14 is an isometric view of one example of a hand-held external unit configured to transmit data to and receive data from an intracranial pressure monitoring device in accordance with FIGS. 1 and 9A-9D.

FIG. 14 illustrates one example of a hand-held device 200 configured to transmit and receive data and control signals from ICP monitoring device 100. Hand-held device 200 includes a housing 202 comprising a transmission end 204 and a handle 206 disposed opposite and coupled to transmission end 204.

Handle 206 of housing 202 can be at least partially hollow such that a replaceable or rechargeable power supply can be stored therein. For example, replaceable or rechargeable batteries can be stored in handle 206 of housing 202 for powering a communication unit disposed within 204. Rechargeable batteries can be recharged by plugging the hand-held unit into a wall outlet via a micro-USB or other physical interface such as a holster that includes metal charging prongs.

In addition to housing transmission circuitry, transmission end 204 of device 200 can include a speaker and/or one or more light emitting diodes ("LED") for providing an audible and/or visual notification to a user that identifies when data is successfully transmitted to or received from ICP monitoring device 100. For example, a single beep may be emitted from a speaker when data is successfully read from and/or transmitted to ICP monitoring device 100, and multiple beeps may be emitted from the speaker when there is an error transmitting or receiving data. Similarly, a green LED may light up when data is correctly transmitted, and a red LED may light up when data an error occurs during transmission.

Additionally, during implantation of the ICP monitoring device 100, device 200 may emit an audible beer or turn on a colored LED to inform the user that the ICP monitoring device 100 has been properly implanted, which may be determined by the ICP monitoring device 100 transmitting an acceptable ICP waveform and/or determining when physical contact has been made with the dura matter, pia matter, or parenchyma. Other methods of providing user feedback, such as a device for vibrating hand-held device 200, may be disposed within and supported by housing 202.

Figure 16:
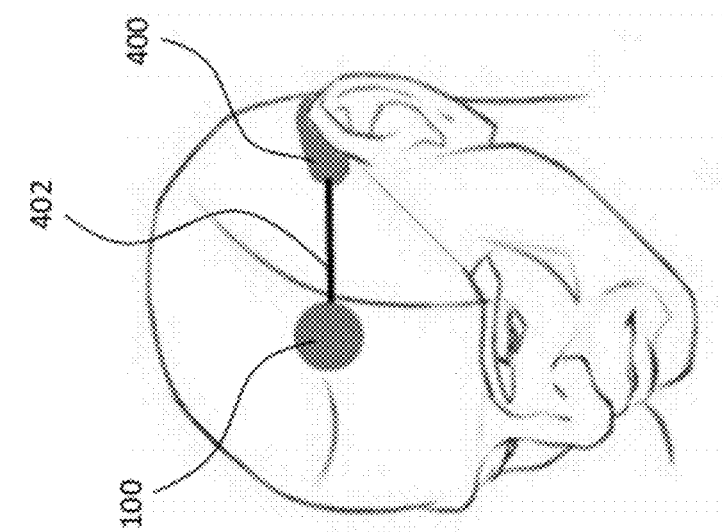
FIG. 16 illustrates an example of an external unit configured to transmit data to and receive data from an intracranial pressure monitoring device in accordance with FIGS. 1 and 9A-9D.
Figure 15:
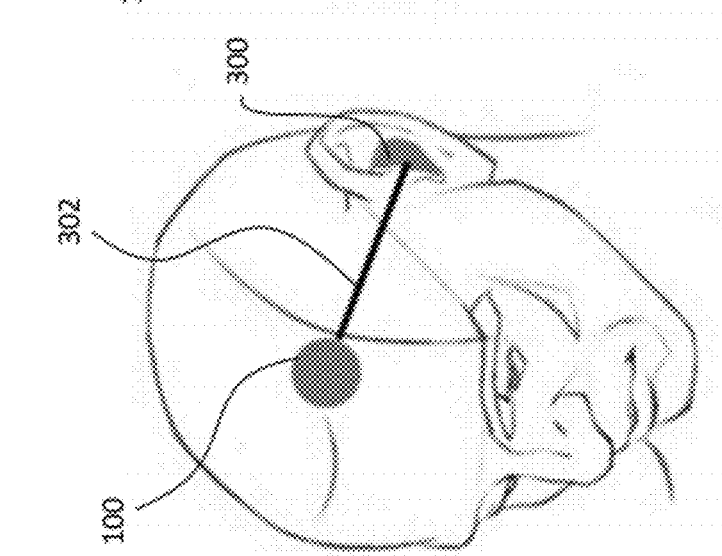
FIG. 15 illustrates an example of an external unit configured to transmit data to and receive data from an intracranial pressure monitoring device in accordance with FIGS. 1 and 9A-9D.

FIGS. 14, 15, and 16 illustrate other possible implementations of external devices 300, 400, 500 that may be used in connection with ICP monitoring device 100. Referring first to FIG. 15, ICP monitoring device 100 is coupled to an external device 300 by a wire 302. External device 300 is configured as an ear piece and is sized and configured to be at least partially received in the ear concha or canal.

Figure 17:
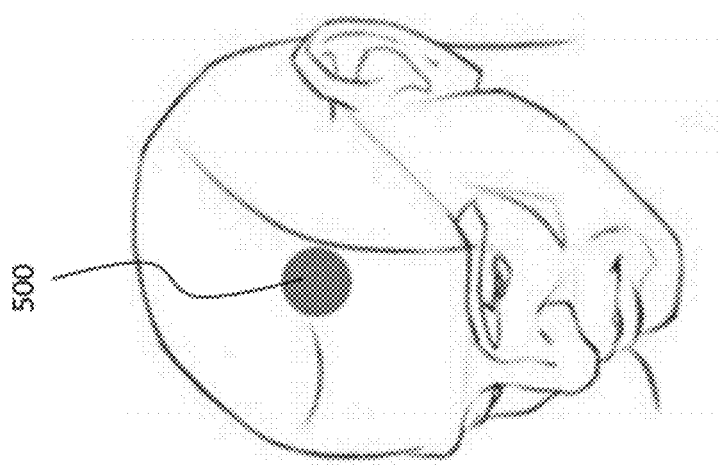
FIG. 17 illustrates an example of an external unit configured to transmit data to and receive data from an intracranial pressure monitoring device in accordance with FIGS. 1 and 9A-9D.

In the embodiment illustrated in FIG. 16, external unit 400 is configured as an ear piece that is configured to fit behind a patient's ear. Unit 400 is coupled to ICP monitoring device 100 via wire 402, which may include a resonant circuit and coil for inductive coupling with coil 188 disposed on PCB 114. In the embodiment illustrated in FIG. 17, external unit 500 is placed directly on the scalp overlying the ICP monitoring device 100. External unit 500 can be secured down with an adhesive or an anchoring stitch.

One of ordinary skill in the art will understand that external devices may take other forms or configurations. For example, an external unit can be integrated into a headband that fits circumferentially around the head. In such an embodiment, the headband can include or more inductive coils such that the orientation of the headband is not crucial to the transmission of power to the implanted ICP monitoring device 100. Other head-worn embodiments include hats. The external device can also be implemented as another worn garment such as a necklace.

In some embodiments, a smartphone or computer peripheral may also be configured as an external device, with an inductive coupling link (i.e., a near-field communication ("NFC") coil) or a 2.4 GHz transceiver (i.e., a Bluetooth transceiver or chip) built-in for powering and/or communicating with the ICP monitoring device 100. In some embodiments, the external device need not be constantly inductively coupled to the ICP monitoring device 100. If the ICP monitoring device 100 is placed in a stand-alone mode as described above, the external device may either receive data periodically when the patient or primary caregiver places it within inductive coupling range, or may receive data more frequently via a longer-range communication protocol such as one implemented in the 2.4 GHz ISM band with a separate antenna 180.

Regardless of the implementation of the external unit 200, 300, 400, 500, such unit may be used in an outpatient setting. As such, the external unit is designed to be rugged and user-friendly, including pre-programmable alarms associated with parameters such as mean ICP, sensor baseline drift, and device failure. In some embodiments, the external units 200, 300, 400, 500 are configured to record symptoms experienced by a patient including, but not limited to, faintness, a headache, a ringing in the ears, etc. The external units 200, 300, 400, 500 are configured to store these time-stamped symptoms alongside the ICP data that were made at the time of the symptom recording in a non-volatile computer storage.

The acquired data can be transmitted in real-time or at a later time to other devices as described in greater detail below. In embodiments in which external units 200, 300, 400, 500 are configured with a display, the external units 200, 300, 400, 500 can display the acquired data, the symptom onset time, and, optionally, the description overlaid on the graph of ICP recordings or derived parameters. Such functionality advantageously allows primary caregivers to correlate the onset of symptoms with certain ICP waveform characteristics, such as an increase in mean ICP.

Figure 18:
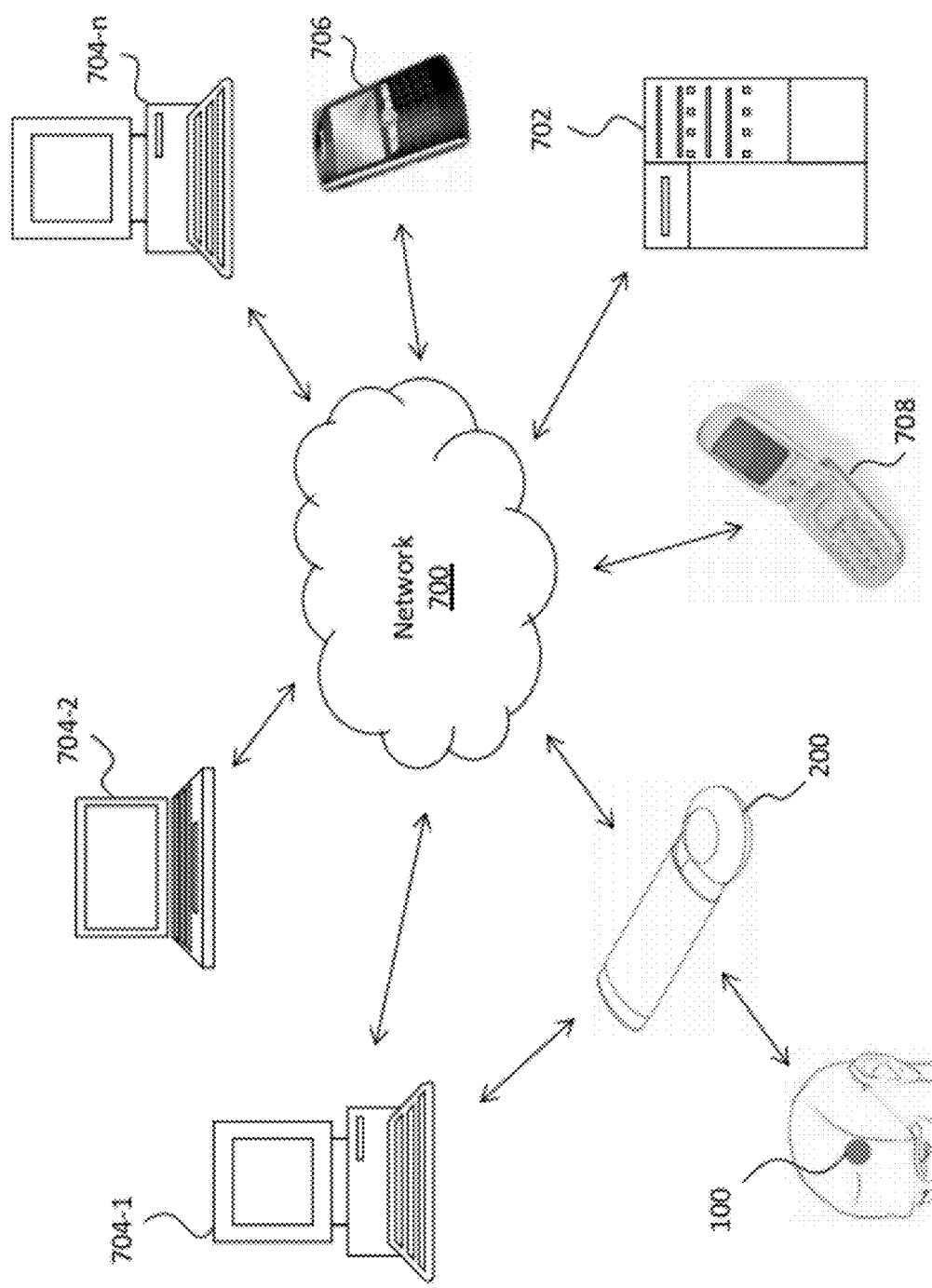
FIG. 18 illustrates one example of a network-based patient monitoring system.

As illustrated in FIG. 18, the external unit(s) 200 are capable of transmitting data over network(s) 700 such as, for example, a local area network ("LAN"), a wide area network ("WAN"), the Internet, an EDGE network, 3G, 4G LTE, or other network over which data can be transmitted. Although only external unit 200 is illustrated in FIG. 18, each of the external units 300, 400, 500 as well as other embodiments that will be apparent to one skilled in the art may be deployed in the system illustrated in FIG. 18 and have the properties and functionality described with reference to hand-held device 200.

In some embodiments, device 200 is configured to receive data from ICP monitoring device 100, as described above, and transmit the data to one or more servers 702 via network 700. For example, device 200 receives data from ICP monitoring device 100 and transmits data to server 702 via network 700 or by first transmitting the data to a computer 704-1, which then transmits the data to server 702. The transmission of data from hand-held device 200 to computer 704-1 can be made via a wireless connection, via a wired connection using a USB connection or other tethered connection, or via an exchange of a memory device such as an SD card or other transferrable memory device.

Various types of data can be stored on server 702, which may also perform data processing functions. In some embodiments, for example, ICP monitoring device 100 transmits raw data (i.e., unprocessed or uncorrelated data) to server 702 via an external device 200, 300, 400, 500. Server 702, which is configured with one or more processors, stores the data in a computer readable storage and performs data processing including the identification one or more waveform features to provide information regarding the condition of the patient. Such conditions include, but are not limited to, a change in intracranial pressure, intracranial compliance, oxygenation, heart rate, temperature, respiratory rate, carotid pressure waveform, peripheral artery waveform, or in cerebral perfusion pressure. As described above, the waveforms can be used to predict rises in ICP, diagnose acute stroke, improve the accuracy in the diagnosis of normal pressure hydrocephalus, and/or assess the responsiveness to a treatment aimed at changing intracranial compliance.

Server 702 is configured to be accessed by primary caregivers and/or device technicians to gauge both the status of patients with implants and the status of the implants themselves. Access to server 702 is made via network 702 from one or more computers 704-1, 704-2, . . . , 704-n ("computers 704"), from a personal digital assistant ("PDA") 706, from a smartphone 708, and/or other device capable of accessing network 700 via a browser or other connection interface. Other examples of network-enabled devices that can access server 702 via network 700 include, but are not limited to, portable music players having Wi-Fi capabilities, tablets, televisions, and Blu-ray players to name a few other possibilities. The network access to server 702 is facilitated by a secure web interface via browser located on the network-enabled device.

The network-enabled devices, e.g., computers 704, PDA 706, phone 708, etc., can be configured to function as a patient monitoring device. For example, server 702 can transmit alarms and/or status updates via network 700 to one or more of the network-enabled devices 704, 706, 708. Such alarms and/or status updates can be transmitted using emails, text messages, automated phone calls, or other communication methods that will be apparent to one of ordinary skill in the art. The status updates and/or alarms can be displayed on a display or trigger an audio alert on the network-enabled devices 704, 706, 708 that function as a patient monitor. As will be understood by one of ordinary skill in the art, the network-enabled devices 704, 706, 708 can reside with the patient, the patient's caregiver, and/or a physician whom the patient might see in an outpatient clinic, urgent care center, or emergency room.

In some embodiments, network-enabled devices 704, 706, 708 that function as patient monitors are capable uploading data to and downloading data from server 702. Examples of data that can be transmitted from a network-enabled device includes, but are not limited to, a patient's physiological parameters, the number and identity of ICP monitoring devices 100 being monitored by the network-enabled device 704, 706, 708, and the software version running on the unit and/or the ICP monitoring unit 100. Additionally, network-enabled devices 704, 706, 708 are configured to download software upgrades and historical data related to a patient's physiological parameters from server 702. Network-enabled devices 704, 706, 708 are also configured to optionally store data received from ICP monitoring unit 100 via external device 200, 300, 400, 500 and/or server 702 internally, or to transmit the downloaded data or data derived from the downloaded data to ICP monitoring unit 100 or server 702.

Network-enabled devices 704, 706, 708 are configured with a processor capable of processing data received from ICP monitoring device 100 via an external unit 200, 300, 400, 500, data received from server 702, or some combination thereof, in certain ways to determine certain parameters for display to a user. These parameters may include an estimation of baseline sensor drift, mean ICP, ICP pulsatility, and other parameters. Devices 704, 706, 708 can display the parameters on the display of the device as a chart, numbers, graphs, annotations overlaid on graphs, or other visual presentation.

As will be understood by one of ordinary skill in the art, network-enabled devices 704, 706, 708 are configured with a user input device, such as a keyboard, a touchscreen for displaying a virtual keyboard, a microphone for receiving audio instructions, camera, or other interface for receiving data from a user. A user can use the user input device to set one or more alarm thresholds related to certain physiological parameters, send commands to an external unit 200, 300, 400, 500 and/or an ICP monitoring device 100, create annotations to be overlaid on graphs of certain physiological parameters, to name a few non-limiting possibilities.

The disclosed devices, methods, and systems advantageously enable the ICP of a patient to be monitored with improved accuracy and with improved intelligence. The incorporation of an accelerometer and/or gyroscope in an ICP monitoring device advantageously enables the ICP monitoring device to determine position-related events such as sleeping, falling, and running, to name a few possibilities. The detection of such position-related events can trigger alerts to caregivers and enables improved diagnostics to be performed on recorded data. For example, the ICP monitoring device can be used to acquire diagnostic measurements for normal pressure hydrocephalus when it is determined that a patient is sleeping.

Waveforms generated from acquired or sensed data can be used to derive actual physiological measurements including, but not limited to, pressure, tissue compliance, or oxygenation. Given that measurement of waveform features is independent of sensor baseline drift, pressure measurement may be achieved without having to extract the sensor for external calibration or use an externally connected pressure reference. Moreover, having a calculated pressure derived from feature based analysis is beneficial in calibration and correction of an actual measured value. The difference between the derived value of pressure or other physiological parameter and the actual measured value can be calculated and the sensor can alert the user if the difference exceeds a specified error threshold, signaling that recalibration may be necessary.

The present devices, systems, and methods can be embodied in the form of methods and apparatus for practicing those methods. The present devices, systems, and methods can also be embodied in the form of program code embodied in a non-transient, tangible media, such as USB flash drives, memory cards, CD-ROMs, DVD-ROMs, Blu-ray disks, hard drives, or any other non-transient machine-readable storage medium, wherein, when the program code is loaded into and executed by a machine, such as a computer, the machine becomes an apparatus for practicing the invention. The present devices, systems, and methods can also be embodied, at least partially, in the form of program code, for example, whether stored in a storage medium, loaded into and/or executed by a machine, or transmitted over some transmission medium, such as over electrical wiring or cabling, through fiber optics, or via electromagnetic radiation, wherein, when the program code is loaded into and executed by a machine, such as a computer, the machine becomes an apparatus for practicing the invention. When implemented on a general-purpose processor, the program code segments combine with the processor to provide a unique device that operates analogously to specific logic circuits.

Although the devices, systems, and methods have been described in terms of exemplary embodiments, they are not limited thereto. Rather, the appended claims should be construed broadly, to include other variants and embodiments of the devices, systems, and methods, which may be made by those skilled in the art without departing from the scope and range of equivalents of the devices, systems, and methods.

What is claimed is:

1. An intracranial pressure monitoring device, comprising:
   a housing defining a first internal chamber, the first internal chamber being hermetically sealed and having controlled contents to produce an internal pressure in the chamber;
   a plurality of strain gauges disposed on an inner surface of a diaphragm defined by a wall of the first internal chamber;
   a device for generating orientation signals; and
   circuitry coupled to the plurality of strain gauges and to the device for generating orientation signals, the circuitry configured to:
      generate intracranial pressure data based at least in part on signals received from the plurality of strain gauges,
      generate orientation data based on the orientation signals received from the device for generating orientation signals;
      store the intracranial pressure data and the orientation data in a computer readable storage such that the intracranial pressure data and orientation data are associated with each other; and
      determine the intracranial pressure based on the association of the intracranial pressure data with the orientation data and on the internal pressure in the first internal chamber.

2. The intracranial pressure monitoring device of claim 1, wherein the circuitry is configured to wirelessly transmit intracranial pressure data and orientation data to a separate device.

3. The intracranial pressure monitoring device of claim 1, wherein the device for generating orientation signals includes at least one of an accelerometer and a gyroscope.

4. The intracranial pressure monitoring device of claim 1, wherein the device and the circuitry are disposed on a printed circuit board disposed in a second chamber defined by the housing.

5. The intracranial pressure monitoring device of claim 1, wherein the device for generating orientation signals and the circuitry are disposed on a printed circuit board disposed in the first internal chamber.

6. The intracranial pressure monitoring device of claim 1, wherein the housing includes a proximal portion and a distal portion, the proximal portion including threads disposed on an exterior surface for engaging bone of a skull.

7. The intracranial pressure monitoring device of claim 6, wherein the distal portion defines a circumferential trough along its length.

8. The intracranial pressure monitoring device of claim 6, wherein the proximal portion and the distal portion are welded together.

9. The intracranial pressure monitoring device of claim 6, wherein the proximal portion and the distal portion are coupled together via a threaded engagement.

10. The intracranial pressure monitoring device of claim 1, wherein the internal pressure within the first internal chamber is less than a pressure outside of the first internal chamber.

11. The intracranial pressure monitoring device of claim 1, wherein the plurality of strain gauges includes:
    first and second strain gauges aligned with each other and disposed adjacent to a radial center of the diaphragm, and
    third and fourth strain gauges aligned with each other and perpendicular to the first and second strain gauges, the third strain gauge disposed between a side wall extending from the diaphragm and the first strain gauge, and the fourth strain gauge disposed between the side wall and the second strain gauge.

12. The intracranial pressure monitoring device of claim 11, wherein the first, second, third, and fourth strain gauges are electrically connected in a Wheatstone bridge.

13. The intracranial pressure monitoring device of claim 12, wherein
    the first and third strain gauges are electrically coupled together at a first node,
    the second and fourth strain gauges are electrically coupled together at a second node,
    the second and third strain gauges are electrically coupled together at a third node set at a first voltage level, and
    the first and fourth strain gauges are electrically coupled together at a fourth node set at a second voltage level.

14. The intracranial pressure monitoring device of claim 13, wherein the circuitry includes a differential amplifier having an output coupled to a processor, the differential processor including a first input coupled to the first node and a second input coupled to the second node.

15. The intracranial pressure monitoring device of claim 11, wherein a first end of the third and fourth strain gauges are aligned with a first axis of the diaphragm, and a second end of the third and fourth strain gauges are aligned with a second axis of the diaphragm, the first and second axes of the diaphragm experience less of one of net compression or net tension than experienced by an area disposed between the first and second axes.

16. The intracranial pressure monitoring device of claim 15, wherein first and second ends of the first and second strain gauges are aligned with the second axis of the diaphragm.

17. The intracranial pressure monitoring device of claim 11, wherein the side wall extends from the diaphragm in a perpendicular direction, and a ridge extends between the side wall and the inner surface of the diaphragm at a non-perpendicular angle with respect to the side wall and the diaphragm.

18. The intracranial pressure monitoring device of claim 1, wherein an external surface of the diaphragm includes a coating for preventing scar tissue overgrowth.

19. The intracranial pressure monitoring device of claim 18, wherein the coating includes at least one of polyvinylpyrrolidone, phosphoryl colene, polyethylene oxide, a hydro-gel, paralene, an anti-inflammatory agent, a cell cycle inhibitor, an anti-platelet agent, an anti-thrombin compound, and a thrombolytic agent.

20. The intracranial pressure monitoring device of claim 1, wherein the circuitry includes an inductive coil and a capacitor, the capacitor configured to store energy in response to receiving a current from the inductive coil.

21. The intracranial pressure monitoring device of claim 1, wherein the diaphragm has a thickness between 0.004 inches and 0.005 inches.

22. The intracranial pressure monitoring device of claim 1, wherein the plurality of strain gauges, the device for generating orientation signals, and the circuitry are all disposed within the hermetically sealed chamber.

23. The intracranial pressure monitoring device of claim 22, wherein the computer readable storage is disposed within the hermetically sealed chamber.

24. The intracranial pressure monitoring device of claim 1, wherein the plurality of strain gauges, the device for generating orientation signals, and the circuitry are all in fluid communication with the hermetically sealed chamber.

25. The intracranial pressure monitoring device of claim 22, wherein the computer readable storage is in fluid communication with the hermetically sealed chamber.

26. The intracranial pressure monitoring device of claim 1, wherein the diaphragm comprises titanium.

27. The intracranial pressure monitoring device of claim 1, wherein the first internal chamber is configured to be coupled with a skull.

28. The intracranial pressure monitoring device of claim 1, wherein the intracranial pressure data and the orientation data are generated simultaneously.

29. The intracranial pressure monitoring device of claim 1, wherein the orientation data is indicative of an orientation of a patient's head.

30. An intracranial pressure monitoring device, comprising:
   a housing defining a first internal chamber and configured to be coupled with a skull, the first internal chamber being hermetically sealed and having controlled contents to produce an internal pressure in the first internal chamber that is less than a pressure outside of the first internal chamber;
   a plurality of strain gauges disposed on an inner surface of a diaphragm defined by a wall of the first internal chamber; and
   circuitry coupled to the plurality of strain gauges, the circuitry configured to generate intracranial pressure data based at least in part on signals received from the plurality of strain gauges and to determine the intracranial pressure,
   wherein the intracranial pressure data is associated with an orientation data, the orientation data indicative of an orientation of the intracranial pressure monitoring device; and
   wherein the intracranial pressure is determined based on the association of the intracranial pressure data with the orientation data and on the internal pressure in the first internal chamber.

* * * * *